(12) United States Patent
Adler et al.

(10) Patent No.: US 7,517,972 B2
(45) Date of Patent: Apr. 14, 2009

(54) NUCLEIC ACID SEQUENCES ENCODING A BITTER TASTE RECEPTOR, T2R76

(75) Inventors: Jon Elliot Adler, San Diego, CA (US); Huixian Tang, San Diego, CA (US); Alexey Pronin, San Diego, CA (US)

(73) Assignee: Senomyx, Inc., San Diego, CA (US)

( * ) Notice: Subject to any disclaimer, the term of this patent is extended or adjusted under 35 U.S.C. 154(b) by 0 days.

(21) Appl. No.: 10/628,464

(22) Filed: Jul. 29, 2003
(Under 37 CFR 1.47)

(65) Prior Publication Data

US 2004/0132134 A1  Jul. 8, 2004

Related U.S. Application Data

(60) Provisional application No. 60/398,727, filed on Jul. 29, 2002.

(51) Int. Cl.
| | | |
|---|---|---|
| *C07H 21/04* | (2006.01) | |
| *C12N 15/63* | (2006.01) | |
| *C12N 1/19* | (2006.01) | |
| *C12N 1/21* | (2006.01) | |
| *C12N 5/16* | (2006.01) | |
| *C12N 5/22* | (2006.01) | |

(52) U.S. Cl. ................. 536/23.5; 435/252.3; 435/254.2; 435/320.1; 435/325; 435/348; 435/364; 435/365; 435/367; 435/369

(58) Field of Classification Search ................. 536/23.5, 536/24.3; 435/69.1, 320.1, 325, 252.3, 348, 435/365, 471
See application file for complete search history.

(56) References Cited

U.S. PATENT DOCUMENTS 5,763,218 A * 6/1998 Fujii et al. ................. 435/69.1
6,004,808 A * 12/1999 Negulescu et al. .......... 435/325

FOREIGN PATENT DOCUMENTS

| WO | WO 99/42470 | 8/1999 |
|---|---|---|
| WO | WO 02257309 A1 * | 7/2002 |
| WO | WO 02068579 A2 * | 9/2002 |

OTHER PUBLICATIONS

Conte et al, 2002 "Identification and characterization of human taste receptor genes belonging to the TAS2R family", Cytogenetic and Genome Research 98: 45-53.*
NCBI Entrez Nucleotide, database record for Locus AC092214, Version AC092214.2, Sep. 15, 2001, 60 pages.*
NCBI Entrez Nucleotide, database record for Locus AC092214, Version AC092214.1, Jun. 29, 2001, 76 pages.*
Baker et al (1997. Nucleic Acids Research. 25(10): 1950-1956).*
Perruccio and Kleinhaus, Society for Neuroscience Abstracts 26(1-2) Abstract No. 66.15, 2000.
Chandrashekar et al., Cell 100(703-711)2000.
Bowie et al., 1990, Science 247:1306-1310.
Alexander et al., Proc. Natl. Acad. Sci. 89(3352-3356)1992.
Hoon et al., Cell 96(541-551)1999.
Lindemann, B. Nature Neuroscience 3(2)99-100, 2000.

* cited by examiner

*Primary Examiner*—Elizabeth C. Kemmerer
*Assistant Examiner*—Zachary C Howard
(74) *Attorney, Agent, or Firm*—Hunton & Williams LLP

(57) ABSTRACT

Isolated nucleic acids encoding T2R76 polypeptides, recombinantly expressed T2R76 polypeptides, heterologous expression systems for recombinant expression of T2R76 polypeptides, assay methods employing the same, and methods for altering taste perception via administration of a T2R76 modulator. These T22R76 polypeptides can be expressed alone or co-expressed with another T2R polypeptide, preferably a different human T2R polypeptide.

20 Claims, No Drawings

NUCLEIC ACID SEQUENCES ENCODING A BITTER TASTE RECEPTOR, T2R76

RELATED APPLICATIONS

This Application claims priority to U.S. Ser. No. 60/398,727 filed on Jul. 29, 2002 which Application is incorporated by reference in its entirety.

FIELD OF THE INVENTION

The present invention generally relates to T2R76 polypeptides and taste perception mediated by the same. More particularly, the present invention provides isolated nucleic acids encoding T2R76 polypeptides, isolated and functional T2R76 polypeptides, a heterologous expression system for recombinant expression of T2R76 polypeptides, methods for identifying modulators of taste perception, especially compounds which are bitter tasting or which block bitter taste, and uses thereof.

DESCRIPTION OF RELATED ART

One of the basic taste modalities that humans can recognize is bitter. Bitter compounds are thought to produce bitter taste by interacting with cell surface receptors. Activation of the receptors initiates intracellular signaling cascades that culminate in neurotransmitter release. Afferent nerve fibers from cranial nerve ganglia then relay the signals to cortical taste centers, where the information is processed as taste perception. These receptors belong to the family of seven transmembrane domain receptors that interact with intracellular G proteins, also called G protein-coupled receptors (GPCRs). See Lindemann (2001) Nature 413(6852): 219-25.

A novel family of GPCRs, termed T2Rs, has been identified in humans and rodents (Adler et al., 2000; Chandrashekar et al., 2000; Matsunami, 2000; PCT International Publication Nos. WO 01/18050 and WO 01/77676). Several lines of evidence suggested that the T2Rs can mediate perception of bitter compounds. First, the T2R genes are specifically expressed in subset of taste receptor cells of the tongue and palate epithelia. Second, T2Rs are genetically linked to loci associated with bitter perception in mice and humans (Conneally et al., 1976; Capeless et al., 1992; Reed et al., 1999; Adler et al., 2000). Third, in vitro studies have shown that T2Rs can activate gustducin, a G protein specifically expressed in taste cells and linked to bitter stimuli transduction (Wong et al., 1996), and that gustducin activation by T2Rs occurs selectively in response to the application of bitter compounds (Chandrashekar et al., 2000). Based on these data, the mT2R and hT2R receptor families are proposed to mediate bitter taste response in mice and human, respectively.

Bitter tastes are often undesirable in food, beverages, oral washes, dentifrices, cosmetics, and pharmaceuticals. A bitter taste can be masked by the addition of sweet compounds, such as sugar; however, the addition of a sweetener may undesirably alter a food flavor and increase calorie intake. In the case of pharmaceuticals, elaborate and costly formulation methods (e.g., coatings and capsules) have been developed to reduce bitter taste upon oral intake. Methods for directly blocking bitter taste via inhibition of taste receptors have not been described.

Thus, there exists a long-felt need in the art to identify and functionally characterize bitter taste receptors as targets for the development of inhibitors of bitter taste perception. To meet this need, the present invention provides novel T2R76 nucleic acids and polypeptides. The present invention also provides methods for identifying and using modulators of T2R76 to alter taste perception.

SUMMARY OF INVENTION

The present invention provides isolated T2R76 nucleic acids and T2R76 polypeptides encoded by the same. The polypeptides and nucleic acids are useful in the detection methods and assays disclosed herein.

A T2R76 nucleic acid can comprise: (a) an isolated nucleic acid molecule encoding a polypeptide of SEQ ID NO:2; (b) an isolated nucleic acid molecule of SEQ ID NO:1; or (c) an isolated nucleic acid molecule substantially similar to SEQ ID NO:1.

A TR76 nucleic acid can also comprise: (a) an isolated nucleic acid molecule encoding a polypeptide of SEQ ID NO:2; (b) an isolated nucleic acid molecule of SEQ ID NO:1; (c) an isolated nucleic acid molecule which hybridizes to a nucleic acid sequence of SEQ ID NO:1 under wash stringency conditions represented by a wash solution having less than about 200 mM salt concentration and a wash temperature of greater than about 45° C., and which encodes a T2R76 polypeptide; or (d) an isolated nucleic acid molecule differing by at least one functionally equivalent codon from the isolated nucleic acid molecule of one of (a), (b), and (c) above in nucleic acid sequence due to the degeneracy of the genetic code, and which encodes a T2R76 polypeptide encoded by the isolated nucleic acid of one of (a), (b), and (c) above. Preferably, an isolated T2R76 nucleic acid comprises: (a) an isolated nucleic acid molecule encoding a polypeptide of SEQ ID NO:2; or (b) an isolated nucleic acid molecule of SEQ ID NO:1.

An isolated T2R76 polypeptide can comprise: (a) a polypeptide of SEQ ID NO:2; (b) a polypeptide substantially identical to SEQ ID NO:2; (c) a polypeptide encoded by a nucleic acid molecule of SEQ ID NO:1; or (d) a polypeptide encoded by a nucleic acid molecule substantially identical to SEQ ID NO:1.

A T2R76 polypeptide can also comprise a polypeptide encoded by an isolated nucleic acid molecule selected from the group consisting of: (a) an isolated nucleic acid molecule encoding a polypeptide of SEQ ID NO:2; (b) an isolated nucleic acid molecule of SEQ ID NO:1; (c) an isolated nucleic acid molecule that hybridizes to a nucleic acid of SEQ ID NO:1 under high stringency conditions, and that encodes a T2R76 polypeptide; and (d) an isolated nucleic acid molecule differing by at least one functionally equivalent codon from the isolated nucleic acid molecule of one of (a), (b), or (c) above in nucleic acid sequence due to the degeneracy of the genetic code, and which encodes a T2R76 polypeptide encoded by the isolated nucleic acid of (a), (b), or (c) above. Preferably, a T2R76 polypeptide comprises SEQ ID NO:2.

The present invention further provides methods for detecting a T2R76 nucleic acid, the method comprising: (a) procuring a biological sample having nucleic acid material; (b) hybridizing an isolated T2R76 nucleic acid molecule under stringent hybridization conditions to the biological sample of (a), thereby forming a duplex structure between the isolated T2R76 nucleic acid and a nucleic acid within the biological sample; and (c) detecting the duplex structure of (b), whereby a T2R 76 nucleic acid molecule is detected.

The present invention further provides antibodies that specifically recognize a T2R76 polypeptide, and methods for producing the same. A representative embodiment of the method comprises: (a) recombinantly or synthetically producing a T2R76 polypeptide; (b) formulating the polypeptide of (a) whereby it is an effective immunogen; (c) administering to an animal the formulation of (b) to generate an immune response in the animal comprising production of antibodies, wherein antibodies are present in the blood serum of the animal; and (d) collecting the blood serum from the animal of (c) comprising antibodies that specifically recognize a T2R76 polypeptide. The disclosed method can further comprise preparing a monoclonal antibody.

Also provided are methods for detecting a level of a T2R76 polypeptide. In a representative embodiment, the method comprises: (a) obtaining a biological sample having peptidic material; (b) detecting a T2R76 polypeptide in the biological sample of (a) by immunochemical reaction with the antibody of the present invention, whereby an amount of T2R76 polypeptide in a sample is determined.

Also provided are systems for recombinant expression of a T2R76 polypeptide. A recombinant expression system can comprise: (a) a T2R76 polypeptide of the invention (e.g., a representative embodiment set forth as SEQ ID NO:2); and (b) a heterologous host cell expressing the T2R76 polypeptide. Additionally, the recumbinant expression system can comprise nucleic acid sequences encoding different T2R polypeptides than T2R76. In particular, the recumbinant espression system may include any of the T2R nucleic acid sequences disclosed in U.S. Pat. No. 6,558,910 issued on May 6, 2003 to Zuker et al, U.S. published application Ser. No. 20020094551, by Adler, John Elliot published Jul. 18, 2002, and U.S. published application Ser. No. 20/030,022,278 by Zuker et al., published on Jan. 30, 2003, all of which are incorporated by reference in their entirety. It should be noted that another name for T2R polypeptides is SF or GR polypeptides, as disclosed in the Zuker Applications incorporated by reference herein. The subject hT2R76 may be expressed with one or more other T2R polypeptides to produce a functional heteromenic taste receptor. The other T2R polypeptides may be another human T2R or T2R of another species, e.g., rat or mouse. A host cell can comprise any suitable cell. A preferred host cell comprises a mammalian cell, more preferably a human cell. Also preferably, a host cell comprises a G protein alpha subunit capable of coupling to a T2R76 polypeptide, for example, a promiscuous G protein such as Gα15, gustducin or transducin.

Using the disclosed system for recombinant expression of a T2R76 polypeptide, the present invention further provides a method for identifying modulators of a T2R76 polypeptide. In a preferred embodiment of the invention, the method comprises: (a) providing a recombinant expression system whereby a T2R76 polypeptide is expressed in a heterologous host cell; (b) providing a test substance to the system of (a); (c) assaying a level or quality of T2R76 function in the presence of the test substance; (d) comparing the level or quality of T2R76 function in the presence of the test substance with a control level or quality of T2R76 function; and (e) identifying a test substance as a T2R76 modulator by determining a level or quality of T2R76 function in the presence of the test substance as significantly changed when compared to a control level or quality of T2R76 function. The assaying can comprise determining an amount of GTPγS binding.

In another embodiment of the invention, a method for identifying a modulator of a T2R76 polypeptide comprises: (a) expressing a T2R76 polypeptide and expressing said polypeptide or polypeptide combinations alone or in combination with one or more other T2R polypeptides to one or more test substances; (b) assaying binding of a test substance to the isolated T2R76 polypeptide or T2R76 containing polypeptide combination; and (c) selecting a candidate substance that demonstrates specific binding to the T2R76 polypeptide.

Also provided are modulators, including agonists and inhibitors of a T2R76 polypeptide, that are identified by the disclosed methods. A modulator can comprise a protein, a peptide, an antibody, a nucleic acid, a small molecule, or combinations thereof. Preferably, a modulator further comprises a modulator of bitter taste perception.

The present invention further provides methods for modulating bitter taste perception in a subject. Preferably, the subject is a mammalian subject, and more preferably a human subject. Also preferably, the bitter taste perception that is altered in a subject comprises a T2R76 function.

In one embodiment of the present invention, a method for modulating bitter taste perception in a subject comprises: (a) preparing a composition comprising a T2R76 modulator identified according to the disclosed methods; and (b) administering an effective dose of the composition to a subject, whereby bitter taste perception in the subject is altered.

For example, the present invention provides methods for reducing bitter taste perception of a bitter compound via co-administering a T2R76 inhibitor and the bitter compound to a subject. The present invention also provides methods for enhancing bitter taste perception of a compound via co-administering a T2R76 agonist and the compound. The co-administering can comprise administering a composition comprising the T2R76 inhibitor admixed with the compound whose taste is to be modulated. In preferred embodiments of the invention, the composition can comprise a food, a beverage, an oral wash, a dentifrice, a cosmetic, or a pharmaceutical.

The present invention also provides methods for enhancing bitter taste perception of a compound via co-administering a T2R76 agonist and the compound whose taste is to be modulated. The T2R76 agonist and the compound can be admixed as a single composition.

Accordingly, it is an object of the present invention to provide novel T2R76 nucleic acids and polypeptides, methods for detecting a T2R76 nucleic acid, heterologous expression systems whereby a T2R76 polypeptide is expressed, methods and assays employing a heterologous T2R76 expression system, and methods for modulating and detecting a T2R76 polypeptide. This object is achieved in whole or in part by the present invention.

An object of the invention having been stated above, other objects and advantages of the present invention will become apparent to those skilled in the art after a study of the following description of the invention and non-limiting Examples.

BRIEF DESCRIPTION OF SEQUENCES IN THE SEQUENCE LISTING

[SEQ ID No: 1 and 2 are human T2R76 nucleotide and amino acid sequences, respectively.

DETAILED DESCRIPTION OF THE INVENTION

I. Definitions

While the following terms are believed to be well understood by one of ordinary skill in the art, the following definitions are set forth to facilitate explanation of the invention.

The terms "a," "an," and "the" are used in accordance with long-standing convention to refer to one or more.

The term "about", as used herein when referring to a measurable value such as a percentage of sequence identity (e.g., when comparing nucleotide and amino acid sequences as described herein below), a nucleotide or protein length, an amount of binding, etc. is meant to encompass variations of ±20% or ±10%, more preferably ±5%, even more preferably ±1%, and still more preferably ±0.1% from the specified amount, as such variations are appropriate to perform a disclosed method or otherwise carry out the present invention.

II. T2R76 Nucleic Acids and Polypeptides

The present invention provides novel T2R76 nucleic acids and novel T2R76 polypeptides, including functional T2R76 polypeptides. A representative T2R76 nucleic acid of the present invention is set forth as SEQ ID NO:1, which encodes the T2R76 polypeptide set forth as SEQ ID NO:2.

The term "T2R76" and terms including "T2R76" (e.g., hT2R76) refer generally to isolated T2R76 nucleic acids, isolated polypeptides encoded by T2R76 nucleic acids, and activities thereof. T2R76 nucleic acids and polypeptides can be derived from any organism. The terms "T2R76" and terms including "T2R76" also refer to polypeptides comprising receptors that are activated by bitter compounds, and to nucleic acids encoding the same. A T2R76 receptor may comprise other T2R polypeptides, and it may be a heteromenic receptor.

The term "isolated", as used in the context of a nucleic acid or polypeptide, indicates that the nucleic acid or polypeptide exists apart from its native environment and is not a product of nature. An isolated nucleic acid or polypeptide can exist in a purified form or can exist in a non-native environment such as a transgenic host cell.

As disclosed further herein below, the present invention also provides a system for functional expression of a T2R76 polypeptide. The system employs a recombinant T2R76 nucleic acid, including SEQ ID NO:1, which may be expressed in association with another T2R nucleic acid.

II.A. T2R76 Nucleic Acids

The terms "nucleic acid molecule" and "nucleic acid" each refer to deoxyribonucleotides or ribonucleotides and polymers thereof in single-stranded, double-stranded, or triplexed form. Unless specifically limited, the term encompasses nucleic acids containing known analogues of natural nucleotides that have similar properties as the reference natural nucleic acid. The terms "nucleic acid molecule" or "nucleic acid" can also be used in place of "gene," "cDNA," "mRNA," or "cRNA." Nucleic acids can be synthesized, or can be derived from any biological source, including any organism. Representative methods for cloning a full-length T2R76 cDNA are described in Example 1.

The term "T2R" or "SF" refers to nucleic acids encoding members of a family of taste-cell specific G protein coupled receptors. These nucleic acids and the polypeptides they encode are referred to as the "T2R", "SF", "GR", or "TAS2R" family of G-protein coupled taste receptors. The members of this (T2R) family are involved in the detection of bitter tastes. Members of the T2R or SF family of taste receptors are disclosed in U.S. Pat. No. 6,558,910; published U.S. Patent Application Ser. No. 200302278 by Zuker et al., published Jan. 20, 2003: and published U.S. Patent Application Ser. No. 20020094551, by Adler, Jon Elliot, published Jul. 18, 20002. Examples of such T2Rs include GR01 (SF01); GR02 (SF02); GR03 (SF03); GR04 (SF04); GR05 (SF05); GR06 (SF06); GR07 (SF07); GR08 (SF08); GR09 (SF09); GR10 (SF10); GR11 (SF11); GR12 (SF1); GR13 (SF13); GR14 (SF14); GR15 (SF15); GR16 (SF16); GR17 (SF17); GR18 (SF18); GR19 (SF19); GR20 (SF20); GR21 (SF21); GR22 (SF22); GR23 (SF23); GR24 (SF24); GR51; T2R55; T2R33; T2R59; T2R61; T2R63; T2R64; T2R65; T2R75; GR25; (SF25); GR26 (SF26); GR27 (SF27); GR28 (SF28); GR29 (SF29); GR30 (SF30 ); GR31 (S F31); GR32 (SF32); GR33 (SF33); GR34 (SF34); GR35 (SF35); GR36 (SF36) GR37 (SF37); GR38 (SF38); GR39 ((SF39); GR40F40); GR41 (SF41); GR42 (SF42); GR43 (SF43); GR 44 (SF44); GR45 (SF45) ; GR46 (SF46); GR47 (SF47) ; GR48 (SF48); GR49 (SF49); and GR50 (SF50).

These T2Rs, SFs, TAS2Rs, et al. or GRs as they are alternatively referred to may be of different species, including human, mouse and rat, and preferably are human. Also encompassed are T2Rs that are "substantially identical" or which possess a specific sequence identity therewith , or which specifically hybridize to any of these sequences as defined infra.

The terms "T2R76" and terms including "T2R76" (e.g., hT2R76) are used herein to refer to nucleic acids that encode a T2R76 polypeptide. Thus, the term "T2R76" refers to isolated nucleic acids of the present invention comprising:

(a) a nucleotide sequence comprising the nucleotide sequence of SEQ ID NO:1; or
(b) a nucleotide sequence substantially identical to SEQ ID NO:1.

The term "substantially identical", as used herein to describe a degree of similarity between nucleotide sequences, refers to two or more sequences that have at least about least 60%, preferably at least about 70%, more preferably at least about 80%, more preferably about 90% to about 99%, still more preferably about 95% to about 99%, and most preferably about 99% nucleotide identity, when compared and aligned for maximum correspondence, as measured using one of the following sequence comparison algorithms or by visual inspection. Preferably, the substantial identity exists in nucleotide sequences of at least about 100 residues, more preferably in nucleotide sequences of at least about 150 residues, and most preferably in nucleotide sequences comprising a full length coding sequence. The term "full length" is used herein to refer to a complete open reading frame encoding a functional T2R76 polypeptide, as described further herein below. Methods for determining percent identity between two polypeptides are defined herein below under the heading "Nucleotide and Amino Acid Sequence Comparisons".

In one aspect, substantially identical sequences can be polymorphic sequences. The term "polymorphic" refers to the occurrence of two or more genetically determined alternative sequences or alleles in a population. An allelic difference can be as small as one base pair.

In another aspect, substantially identical sequences can comprise mutagenized sequences, including sequences comprising silent mutations. A mutation can comprise one or more residue changes, a deletion of residues, or an insertion of additional residues.

Another indication that two nucleotide sequences are substantially identical is that the two molecules hybridize specifically to or hybridize substantially to each other under stringent conditions. In the context of nucleic acid hybridization, two nucleic acid sequences being compared can be designated a "probe" and a "target." A "probe" is a reference nucleic acid molecule, and a "target" is a test nucleic acid molecule, often found within a heterogeneous population of nucleic acid molecules. A "target sequence" is synonymous with a "test sequence."

A preferred nucleotide sequence employed for hybridization studies or assays includes probe sequences that are complementary to or mimic at least an about 14 to 40 nucleotide sequence of a nucleic acid molecule of the present invention. Preferably, probes comprise 14 to 20 nucleotides, or even longer where desired, such as 30, 40, 50, 60, 100, 200, 300, or 500 nucleotides or up to the full length of any SEQ ID NO:1. Such fragments can be readily prepared by, for example, chemical synthesis of the fragment, by application of nucleic acid amplification technology, or by introducing selected sequences into recombinant vectors for recombinant production.

The phrase "hybridizing specifically to" refers to the binding, duplexing, or hybridizing of a molecule only to a particular nucleotide sequence under stringent conditions when that sequence is present in a complex nucleic acid mixture (e.g., total cellular DNA or RNA).

The phrase "hybridizing substantially to" refers to complementary hybridization between a probe nucleic acid molecule and a target nucleic acid molecule and embraces minor mismatches that can be accommodated by reducing the stringency of the hybridization media to achieve the desired hybridization.

"Stringent hybridization conditions" and "stringent hybridization wash conditions" in the context of nucleic acid hybridization experiments such as Southern and Northern blot analysis are both sequence- and environment-dependent. Longer sequences hybridize specifically at higher temperatures. An extensive guide to the hybridization of nucleic acids is found in Tijssen (1993) *Laboratory Techniques in Biochemistry and Molecular Biology-Hybridization with Nucleic Acid* Probes, part I chapter 2, Elsevier, New York, N.Y. Generally, highly stringent hybridization and wash conditions are selected to be about 50° C. lower than the thermal melting point (Tm) for the specific sequence at a defined ionic strength and pH. Typically, under "stringent conditions" a probe will hybridize specifically to its target subsequence, but to no other sequences.

The Tm is the temperature (under defined ionic strength and pH) at which 50% of the target sequence hybridizes to a perfectly matched probe. Very stringent conditions are selected to be equal to the Tm for a particular probe. An example of stringent hybridization conditions for Southern or Northern Blot analysis of complementary nucleic acids having more than about 100 complementary residues is overnight hybridization in 50% formamide with 1 mg of heparin at 42° C. An example of highly stringent wash conditions is 15 minutes in 0.1×SSC at 65° C. An example of stringent wash conditions is 15 minutes in 0.2×SSC buffer at 65° C. See Sambrook et al., eds (1989) *Molecular Cloning: A Laboratory Manual*, Cold Spring Harbor Laboratory Press, Cold Spring Harbor, N.Y. for a description of SSC buffer. Often, a high stringency wash is preceded by a low stringency wash to remove background probe signal. An example of medium stringency wash conditions for a duplex of more than about 100 nucleotides, is 15 minutes in 1×SSC at 45° C. An example of low stringency wash for a duplex of more than about 100 nucleotides, is 15 minutes in 4× to 6×SSC at 40° C. For short probes (e.g., about 10 to 50 nucleotides), stringent conditions typically involve salt concentrations of less than about 1 M Na+ ion, typically about 0.01 to 1 M Na$^+$ ion concentration (or other salts) at pH 7.0-8.3, and the temperature is typically at least about 30° C. Stringent conditions can also be achieved with the addition of destabilizing agents such as formamide. In general, a signal to noise ratio of 2-fold (or higher) than that observed for an unrelated probe in the particular hybridization assay indicates detection of a specific hybridization.

The following are examples of hybridization and wash conditions that can be used to identify nucleotide sequences that are substantially identical to reference nucleotide sequences of the present invention: a probe nucleotide sequence preferably hybridizes to a target nucleotide sequence in 7% sodium dodecyl sulphate (SDS), 0.5M NaP04, 1 mM EDTA at 50° C. followed by washing in 2×SSC, 0.1% SDS at 50° C.; more preferably, a probe and target sequence hybridize in 7% sodium dodecyl sulphate (SDS), 0.5M NaP04, 1 mM EDTA at 50° C. followed by washing in 1×SSC, 0.1% SDS at 50° C.; more preferably, a probe and target sequence hybridize in 7% sodium dodecyl sulphate (SDS), 0.5M NaP04, 1 mM EDTA at 50° C. followed by washing in 0.5×SSC, 0.1% SDS at 50° C.; more preferably, a probe and target sequence hybridize in 7% sodium dodecylsulphate (SDS), 0.5M NaP04, 1 mM EDTA at 50° C. followed by washing in 0.1×SSC, 0.1% SDS at 50° C.; more preferably, a probe and target sequence hybridize in 7% sodium dodecyl sulphate (SDS), 0.5M NaP04, 1 mM EDTA at 50° C. followed by washing in 0.1×SSC, 0.1% SDS at 65° C.

A further indication that two nucleic acid sequences are substantially identical is that proteins encoded by the nucleic acids are substantially identical, share an overall three-dimensional structure, or are biologically functional equivalents. These terms are defined further under the heading "T2R76 Polypeptides" herein below. Nucleic acid molecules that do not hybridize to each other under stringent conditions are still substantially identical if the corresponding proteins are substantially identical. This can occur, for example, when two nucleotide sequences comprise conservatively substituted variants as permitted by the genetic code.

The term "conservatively substituted variants" refers to nucleic acid sequences having degenerate codon substitutions wherein the third position of one or more selected (or all) codons is substituted with mixed-base and/or deoxyinosine residues. See Batzer et al. (1991) Nucleic Acids Res 19:5081; Ohtsuka et al. (1985) J Biol Chem 260:2605-2608; and Rossolini et al. (1994) *Mol Cell Probes* 8:91-98.

The term "T2R" also encompasses nucleic acids comprising subsequences and elongated sequences of a T2R nucleic acid, preferably T2R76 including nucleic acids complementary to a T2R nucleic acid, T2R RNA molecules, and nucleic acids complementary to T2R RNAs (cRNAs).

The term "subsequence" refers to a sequence of nucleic acids that comprises a part of a longer nucleic acid sequence. An exemplary subsequence is a probe, described herein above, or a primer. The term "primer" as used herein refers to a contiguous sequence comprising about 8 or more deoxyribonucleotides or ribonucleotides, preferably 10-20 nucleotides, and more preferably 20-30 nucleotides of a selected nucleic acid molecule. The primers of the invention encompass oligonucleotides of sufficient length and appropriate sequence so as to provide initiation of polymerization on a nucleic acid molecule of the present invention.

The term "elongated sequence" refers to an addition of nucleotides (or other analogous molecules) incorporated into the nucleic acid. For example, a polymerase (e.g., a DNA polymerase) can add sequences at the 3' terminus of the nucleic acid molecule. In addition, the nucleotide sequence can be combined with other DNA sequences, such as promoters, promoter regions, enhancers, polyadenylation signals, intronic sequences, additional restriction enzyme sites, multiple cloning sites, and other coding segments.

The term "complementary sequences," as used herein, indicates two nucleotide sequences that comprise antiparallel nucleotide sequences capable of pairing with one another upon formation of hydrogen bonds between base pairs. As used herein, the term "complementary sequences" means nucleotide sequences which are substantially complementary, as can be assessed by the same nucleotide comparison methods set forth below, or is defined as being capable of hybridizing to the nucleic acid segment in question under relatively stringent conditions such as those described herein. A particular example of a complementary nucleic acid segment is an antisense oligonucleotide.

The present invention also provides chimeric genes comprising the disclosed T2R76 nucleic acids and recombinant T2R76 nucleic acids. Thus, also included are constructs and vectors comprising T2R76 nucleic acids, optionally expressed in combination with other T2R nucleic acids.

The term "gene" refers broadly to any segment of DNA associated with a biological function. A gene encompasses sequences including but not limited to a coding sequence, a promoter region, a cis-regulatory sequence, a non-expressed DNA segment that is a specific recognition sequence for regulatory proteins, a non-expressed DNA segment that contributes to gene expression, a DNA segment designed to have desired parameters, or combinations thereof. A gene can be obtained by a variety of methods, including cloning from a biological sample, synthesis based on known or predicted sequence information, and recombinant derivation of an existing sequence.

The term "chimeric gene," as used herein, refers to a promoter region operatively linked to a T2R sequence, e.g., a T2R cDNA, a T2R nucleic acid encoding an antisense RNA molecule, a T2R nucleic acid encoding an RNA molecule having tertiary structure (e.g., a hairpin structure) or a T2R nucleic acid encoding a double-stranded RNA molecule. The term "chimeric gene" also refers to a T2R promoter region operatively linked to a heterologous sequence. Preparation of a chimeric gene of the present invention is described in Example 2. Preferably, the T2R is T2R76.

The term "operatively linked", as used herein, refers to a functional combination between a promoter region and a nucleotide sequence such that the transcription of the nucleotide sequence is controlled and regulated by the promoter region. Techniques for operatively linking a promoter region to a nucleotide sequence are known in the art.

The term "recombinant" generally refers to an isolated nucleic acid that is replicable in a non-native environment. Thus, a recombinant nucleic acid can comprise a non-replicable nucleic acid in combination with additional nucleic acids, for example vector nucleic acids, that enable its replication in a host cell.

The term "vector" is used herein to refer to a nucleic acid molecule having nucleotide sequences that enable its replication in a host cell. A vector can also include nucleotide sequences to permit ligation of nucleotide sequences within the vector, wherein such nucleotide sequences are also replicated in a host cell. Representative vectors include plasmids, cosmids, and viral vectors. A vector can also mediate recombinant production of a T2R76 polypeptide, as described further herein below.

The term "construct", as used herein to describe a type of construct comprising an expression construct, refers to a vector further comprising a nucleotide sequence operatively inserted with the vector, such that the nucleotide sequence is recombinantly expressed.

The terms "recombinantly expressed" or "recombinantly produced" are used interchangeably to refer generally to the process by which a polypeptide encoded by a recombinant nucleic acid is produced.

Thus, preferably recombinant T2R, nucleic acides, i.e., T2R76 nucleic acids comprise heterologous nucleic acids. The term "heterologous nucleic acids" refers to a sequence that originates from a source foreign to an intended host cell or, if from the same source, is modified from its original form. A heterologous nucleic acid in a host cell can comprise a nucleic acid that is endogenous to the particular host cell but has been modified, for example by mutagenesis or by isolation from native cis-regulatory sequences. A heterologous nucleic acid also includes non-naturally occurring multiple copies of a native nucleotide sequence. A heterologous nucleic acid can also comprise a nucleic acid that is incorporated into a host cell's nucleic acids at a position wherein such nucleic acids are not ordinarily found.

Nucleic acids of the present invention can be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions are also known in the art. See e.g., Sambrook et al. (eds.) (1989) *Molecular Cloning Laboratory Manual*. Cold Spring Harbor Laboratory Press, Cold Spring Harbor, N.Y.; Silhavy et al. (1984) *Experiments with Gene Fusions*. Cold Spring Harbor Laboratory Press, Cold Spring Harbor, N.Y.; Glover & Hames (1995) *DNA Cloning: A Practical Approach,* 2nd ed. IRL Press at Oxford University Press, Oxford/New York; Ausubel (ed.) (1995) *Short Protocols in Molecular Biology*, 3rd ed. Wiley, New York.

III.B. T2R76 Pollypeptides

The present invention provides novel T2R76 polypeptides, a representative embodiment of which is set forth as SEQ ID NOs:2. Preferably, an isolated T2R76 polypeptide of the present invention comprises a recombinantly expressed T2R76 polypeptide. Also preferably, isolated T2R76 polypeptides comprise functional T2R76 polypeptides. These T2R76 polypeptides may be expressed in combination with one or more other T2R polypeptides.

Thus, novel T2R76 polypeptides useful in the methods of the present invention comprise: (a) a polypeptide of SEQ ID NO:2; (b) a polypeptide substantially identical to SEQ ID NO:2; (c) a polypeptide encoded by a nucleic acid molecule of SEQ ID NO:1; or (d) a polypeptide encoded by a nucleic acid molecule substantially identical to SEQ ID NO:1. A T2R76 polypeptide can also comprise: (a) an isolated nucleic acid molecule encoding a polypeptide of SEQ ID NO:2; (b) an isolated nucleic molecule of SEQ ID NO:1; (c) an isolated nucleic acid molecule which hybridizes to a T2R76 nucleic acid sequence under wash stringency conditions represented by a wash solution having less than about 200 mM salt concentration and a wash temperature of greater than about 45° C., and which encodes a T2R76 polypeptide; and (d) an isolated nucleic acid molecule differing by at least one functionally equivalent codon from the isolated nucleic acid molecule of one of (a), (b), and (c) above in nucleic acid sequence due to the degeneracy of the genetic code, and which encodes a T2R76 polypeptide encoded by the isolated nucleic acid of one of (a), (b), and (c) above.

The term "substantially identical", as used herein to describe a level of similarity between a T2R and a protein substantially identical thereto, refers to a protein that is at least 35% identical thereto. For example, in the case of T2R76 and a protein substantially identical to this T2R76 protein, this refers to a sequence that is at least about 35% identical to SEQ ID NO:2, when compared over the full length of a T2R76 protein. Preferably, a protein substantially identical to a T2R76 protein comprises an amino acid sequence that is at least about 35% to about 45% identical to SEQ ID NO:2, more preferably at least about 45% to about 55% identical to SEQ ID NO:2, even more preferably at least about 55% to about 65% identical to SEQ ID NO:2, still more preferably at least about 65% to about 75% identical to SEQ ID NO:2, still more preferably at least about 75% to about 85% identical to SEQ ID NO:2, still more preferably at least about 85% to about 95% identical to SEQ ID NO:2, and still more preferably at least about 95% to about 99% identical to SEQ ID NO:2 when compared over the full length of a T2R76 polypeptide. The term "full length" refers to a functional T2R76 polypeptide, as described further herein below. Methods for determining percent identity between two polypeptides are also defined herein below under the heading "Nucleotide and Amino Acid Sequence Comparisons".

The term "substantially identical," when used to describe polypeptides, also encompasses two or more polypeptides sharing a conserved three-dimensional structure. Computational methods can be used to compare structural representations, and structural models can be generated and easily tuned to identify similarities around important active sites or ligand binding sites. See Saqi et al. (1999) *Bioinformatics* 15:521-522; Barton (1998) *Acta Crystallogr D Biol Crystallogr* 54:1139-1146; Henikoff et al. (2000) *Electrophoresis* 21:1700-1706; and Huang et al. (2000) *Pac Symp Biocomput*: 230-241.

Substantially identical proteins also include proteins comprising amino acids that are functionally equivalent to amino acids of SEQ ID NO:2. The term "functionally equivalent" in the context of amino acids is known in the art and is based on the relative similarity of the amino acid side-chain substituents. See Henikoff & Henikoff (2000) Adv Protein Chem 54:73-97. Relevant factors for consideration include side-chain hydrophobicity, hydrophilicity, charge, and size. For example, arginine, lysine, and histidine are all positively charged residues; that alanine, glycine, and serine are all of similar size; and that phenylalanine, tryptophan, and tyrosine all have a generally similar shape. By this analysis, described further herein below, arginine, lysine, and histidine; alanine, glycine, and serine; and phenylalanine, tryptophan, and tyrosine; are defined herein as biologically functional equivalents.

In making biologically functional equivalent amino acid substitutions, the hydropathic index of amino acids can be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine (+2.5); methionine (+1.9); alanine (+1.8); glycine 0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9) and arginine (4.5).

The importance of the hydropathic amino acid index in conferring interactive biological function on a protein is generally understood in the art (Kyte et al., 1982). It is known that certain amino acids can be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101 describes that the greatest local average hydrophilicity of a protein, as governed by the hydrophilicity of its adjacent amino acids, correlates with its immunogenicity and antigenicity, e.g., with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

The term "substantially identical" also encompasses polypeptides that are biologically functional equivalents of a T2R polypeptide e.g., T2R76 polypeptide. The term "functional" includes an activity of an T2R76 polypeptide, for example activating intracellular signaling pathways (e.g., coupling with gustducin) and mediating taste perception. Preferably, such activation shows a magnitude and kinetics that are substantially similar to that of a cognate T2R polypeptide, e.g., T2R76 polypeptide in vivo. Representative methods for assessing T2R76 activity are described herein below.

The present invention also provides functional fragments of a T2R76 polypeptide. Such functional portion need not comprise all or substantially all of the amino acid sequence of a native T2R76 gene product.

The present invention also includes functional polypeptide sequences that are longer sequences than that of a native T2R polypeptide e.g., T2R76 polypeptide. For example, one or more amino acids can be added to the N-terminus or C-terminus of a T2R polypeptide e.g., T2R76 polypeptide. Such additional amino acids can be employed in a variety of applications, including but not limited to purification applications. Methods of preparing elongated proteins are known in the art.

II.C. Nucleotide and Amino Acid Sequence Comparisons

The terms "identical" or "percent identity" in the context of two or more nucleotide or polypeptide sequences, refer to two or more sequences or subsequences that are the same or have a specified percentage of amino acid residues or nucleotides that are the same, when compared and aligned for maximum correspondence, as measured using one of the sequence comparison algorithms disclosed herein or by visual inspection.

The term "substantially identical" in regards to a nucleotide or polypeptide sequence means that a particular sequence varies from the sequence of a naturally occurring sequence by one or more deletions, substitutions, or additions, the net effect of which is to retain. biological function of a T2R nucleic acid or polypeptide e.g., T2R76 nucleic acid or a T2R76 polypeptide.

For comparison of two or more sequences, typically one sequence acts as a reference sequence to which one or more test sequences are compared. When using a sequence comparison algorithm, test and reference sequences are entered into a computer program, subsequence coordinates are designated if necessary, and sequence algorithm program parameters are selected. The sequence comparison algorithm then calculates the percent sequence identity for the designated test sequence(s) relative to the reference sequence, based on the selected program parameters.

Optimal alignment of sequences for comparison can be conducted, for example, by the local homology algorithm of Smith & Waterman (1981) *Adv Appl Math* 2:482-489, by the homology alignment algorithm of Needleman & Wunsch (1970) *J Mol Biol* 48:443-453, by the search for similarity method of Pearson & Lipman (1988) *Proc Natl Acad Sci USA* 85:2444-2448, by computerized implementations of these algorithms (GAP, BESTFIT, FASTA, and TFASTA in the Wisconsin Genetics Software Package, Genetics Computer Group, Madison, Wis.), or by visual inspection. See generally, Ausubel (ed.) (1995) *Short Protocols in Molecular Biology*, 3rd ed. Wiley, New York.

A preferred algorithm for determining percent sequence identity and sequence similarity is the BLAST algorithm, which is described in Altschul et al. (1990) *J Mol Biol* 215: 403-410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of-the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength W=11, an expectation E=10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. See Henikoff & Henikoff (11992) *Proc Natl Acad Sci USA* 89:10915-10919.

In addition to calculating percent sequence identity, the BLAST algorithm also performs a statistical analysis of the similarity between two sequences. See e.g., Karlin & Altschul (1993) *Proc Natl Acad Sci USA* 90:5873-5877. One measure of similarity provided by the BLAST algorithm is the smallest sum probability (P(N)), which provides an indication of the probability by which a match between two nucleotide or amino acid sequences that would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

III Methods for Detecting a T2R76 Nucleic Acid

In another aspect of the invention, a method is provided for detecting a nucleic acid molecule that encodes a T2R76 polypeptide. Such methods can be used to detect T2R76 gene variants or altered gene expression. For example, detection of a change in T2R76 sequence or expression can be used for diagnosis of T2R76-related differences in taste perception. Preferably, a nucleic acid used for this method comprises the sequence of SEQ ID NO:1.

Sequences detected by methods of the invention can detected, subcloned, sequenced, and further evaluated by any measure well known in the art using any method usually applied to the detection of a specific DNA sequence. Thus, the nucleic acids of the present invention can be used to clone genes and genomic DNA comprising the disclosed sequences. Alternatively, the nucleic acids of the present invention can be used to clone genes and genomic DNA of related sequences. Using the nucleic acid sequences disclosed herein, such methods are known to one skilled in the art. See e.g., Sambrook et al., eds (1989) *Molecular Cloning*, Cold Spring Harbor Laboratory Press, Cold Spring Harbor, N.Y. Representative methods are also disclosed in Examples 1-4.

In one embodiment of the invention, levels of a T2R76 nucleic acid molecule are measured by, for example, using an RT-PCR assay. See Chiang (1998) *J Chromatogr A* 806:209-218, and references cited therein.

In another embodiment of the invention, genetic assays based on nucleic acid molecules of the present invention can be used to screen for genetic variants, for example by allele-specific oligonucleotide (ASO) probe analysis (Conner et al., 1983), oligonucleotide ligation assays (OLAs) (Nickerson et al., 1990), single-strand conformation polymorphism (SSCP) analysis (Orita et al., 1989), SSCP/heteroduplex analysis, enzyme mismatch cleavage, direct sequence analysis of amplified exons (Kestila et al., 1998; Yuan et al., 1999), allele-specific hybridization (Stoneking et al., 1991), and restriction analysis of amplified genomic DNA containing the specific mutation. Automated methods can also be applied to large-scale characterization of single nucleotide polymorphisms (Wang et al., 1998; Brookes, 1999). Preferred detection methods are non-electrophoretic, including, for example, the TAQ-MAN™ allelic discrimination assay, PCR-OLA, molecular beacons, padlock probes, and well fluorescence. See Landegren et al. (1998) *Genome Res* 8:769-776 and references cited therein.

IV. System for Recombinant Expression of a T2R76 Polypeptide

The present invention further provides a system for expression of a recombinant T2R76 polypeptide of the present invention. This TR276 polypeptide may be expressed with one or more other T2Rs which may be human or non-human T2Rs. Such a system can be used for subsequent purification and/or characterization of a T2R76 polypeptide. For example, a purified T2R76 polypeptide can be used as an immunogen for the production of an T2R76 antibody, described further herein below.

A system for recombinant expression of a T2R76 polypeptide can also be used for the identification of modulators of a T2R76 polypeptide. Alternatively, the disclosed T2R76 polypeptides can be used as a control polypeptide when assaying the activation of other test polypeptides. Such test polypeptides can include other T2Rs that are implicated in taste perception, for example any one of those polypeptides disclosed in Adler et al. (2000) *Cell* 100:693-702 and in Matsunami et al. (2000) *Nature* 601-603.

The term "expression system" refers to a host cell comprising a heterologous nucleic acid and the polypeptide encoded by the heterologous nucleic acid. For example, a heterologous expression system can comprise a host cell transfected with a construct comprising a recombinant T2R76 nucleic acid, a host cell transfected with T2R76 cRNA, or a cell line produced by introduction of heterologous nucleic acids into a host cell genome. As noted, these expression systems may include other T2R nucleic acids.

A system for recombinant expression of a T2R76 polypeptide can comprise: (a) a recombinantly expressed T2R76 polypeptide; and (b) a host cell comprising the recombinantly expressed T2R76 polypeptide. For example, a T2R76 cRNA can be transcribed in vitro and then introduced into a host cell, whereby a T2R76 polypeptide is expressed. The system can further comprise one or more additional T2R polypeptides, in order to produce a heteromenic T2R receptor comprising hT2R76 and another T2R polypeptide.

A system for recombinant expression of a T2R76 polypeptide can also comprise: (a) a construct comprising a vector and a nucleic acid molecule encoding a T2R76 polypeptide operatively linked to a heterologous promoter; and (b) a host cell comprising the construct of (a), whereby the host cell expresses a T2R76 polypeptide. The system can further comprise constructs encoding one or more additional T2R polypeptides. Additionally, a single construct itself can encode a T2R76 polypeptide and one or more additional T2R polypeptides.

Isolated polypeptides and recombinantly produced polypeptides can be purified and characterized using a variety of standard techniques that are known to the skilled artisan. See e.g., Schröder & Lübke (1965) *The Peptides*. Academic Press, New York; Schneider & Eberle (1993) *Peptides, 1992: Proceedings of the Twenty-Second European Peptide Symposium, Sep.* 13-19, 1992, *Interlaken, Switzerland*. Escom, Leiden; Bodanszky (1993) *Principles of Peptide Synthesis*, 2nd rev. ed. Springer-Verlag, Berlin/New York; Ausubel (ed.) (1995) *Short Protocols in Molecular Biolog*, 3rd ed. Wiley, New York.

Preferably, a recombinantly expressed T2R76 polypeptide comprises a functional taste receptor, more preferably a bitter taste receptor. Thus, a recombinantly expressed T2R76 polypeptide preferably displays activation in response to bitter compounds. Also preferably, a recombinant T2R76 polypeptide shows activation responses similar to a native T2R76 polypeptide. Representative methods for determining T2R76 function are described herein below.

IV.A. Expression Constructs

A construct for expression of a T2R76 polypeptide includes a vector and a T2R76 nucleotide sequence, wherein the T2R76 nucleotide sequence is operatively linked to a promoter sequence. A construct for recombinant T2R76 expression can also comprise transcription termination signals and sequences required for proper translation of the nucleotide sequence. Preparation of an expression construct, including addition of translation and termination signal sequences, is known to one skilled in the art.

Recombinant production of a T2R polypeptide, e.g., T2R76 polypeptide can be directed using a constitutive promoter or an inducible promoter. Representative promoters that can be used in accordance with the present invention include Simian virus 40 early promoter, a long terminal repeat promoter from retrovirus, an actin promoter, a heat shock promoter, and a metallothien protein.

Suitable vectors that can be used to express a T2R76 polypeptide include but are not limited to viruses such as vaccinia virus or adenovirus, baculovirus vectors, yeast vectors, bacteriophage vectors (e.g., lambda phage), plasmid and cosmid DNA vectors, transposon-mediated transformation vectors, and derivatives thereof.

Constructs are introduced into a host cell using a transfection method compatible with the vector employed. Standard transfection methods include electroporation, DEAE-Dextran transfection, calcium phosphate precipitation, liposome-mediated transfection, transposon-mediated transformation, infection using a retrovirus, particle-mediated gene transfer, hyper-velocity gene transfer, and combinations thereof.

IV.B. Host Cells

The term "host cell", as used herein, refers to a cell into which a heterologous nucleic acid molecule can be introduced. Any suitable host cell can be used, including but not limited to eukaryotic hosts such as mammalian cells (e.g., HEK-293 cells, HeLa cells, CV-1 cells, COS cells), amphibian cells (e.g., *Xenopus oocytes*), insect cells (e.g., Sf9 cells), as well as prokaryotic hosts such as *E. coli* and *Bacillus subtilis*. Preferred host cells substantially lack a T2R76 polypeptide.

A host cell strain can be chosen which modulates the expression of the recombinant sequence, or modifies and processes the gene product in the specific fashion desired. For example, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system can be used to produce a non-glycosylated core protein product, and expression in yeast will produce a glycosylated product.

The present invention further encompasses recombinant expression of a T2R76 polypeptide in a stable cell line. Methods for generating a stable cell line following transformation of a heterologous construct into a host cell are known in the art. See e.g., Joyner (1993) *Gene Tarneting: A Practical Approach*. Oxford University Press, Oxford/New York. Thus, transformed cells, tissues, or non-human organisms are understood to encompass not only the end product of a transformation process, but also transgenic progeny or propagated forms thereof.

The present invention further encompasses cryopreservation of cells expressing a recombinant T2R76 polypeptide as disclosed herein. Thus, transiently transfected cells and cells of a stable cell line expressing T2R76 can be frozen and stored for later use. Frozen cells can be readily transported for use at a remote location.

Cryopreservation media generally consists of a base medium, cryopreservative, and a protein source. The cryopreservative and protein protect the cells from the stress of the freeze-thaw process. For serum-containing medium, a typical cryopreservation medium is prepared as complete medium containing 10% glycerol; complete medium containing 10% DMSO (dimethylsulfoxide), or 5.0% cell-conditioned medium with 50% fresh medium with 10% glycerol or 10% DMSO. For serum-free medium, typical cryopreservation formulations include 50% cell-conditioned serum free medium with 50% fresh serum-free medium containing 7.5% DMSO; or fresh serum-free medium containing 7.5% DMSO and 10% cell culture grade DMSO. Preferably, a cell suspension comprising about 106 to about 107 cells per ml is mixed with cryopreservation medium.

Cells are combined with cryopreservation medium in a vial or other container suitable for frozen storage, for example NUNC@ CRYOTUBESTM (available from Applied Scientific of South San Francisco, Calif.). Cells can also be aliquotted to wells of a multi-well plate, for example a 96-well plate designed for highthroughput assays, and frozen in plated format.

Cells are preferably cooled from room temperature to a storage temperature at a rate of about −1° C. per minute. The cooling rate can be controlled, for example, by placing vials containing cells in an insulated water-filled reservoir having about 1 liter liquid capacity, and placing such cube in a −70° C. mechanical freezer. Alternatively, the rate of cell cooling can be controlled at about −1° C. per minute by submersing vials in a volume of liquid refrigerant such as an aliphatic alcohol, the volume of liquid refrigerant being more than fifteen times the total volume of cell culture to be frozen, and placing the submersed culture vials in a conventional freezer at a temperature below about −70° C. Commercial devices for freezing cells are also available, for example, the Planer Mini-Freezer R202/200R (Planer Products Ltd. of Great Britain) and the BF-5 Biological Freezer (Union Carbide Corporation of Danbury, Conn., United States of America). Preferably, frozen cells are stored at or below about −70° C. to about −80° C., and more preferably at or below about −130° C.

To obtain the best possible cell survival, thawing of the cells must be performed as quickly as possible. Once a vial, or other reservoir containing frozen cells is removed from storage, it should be placed directly into a 37° C. water bath and gently shaken until it is completely thawed. If cells are particularly sensitive to cryopreservatives, the cells are centrifuged to remove cryopreservative prior to further growth.

Additional methods for preparation and handling of frozen cells can be found in Freshney (1987) *Culture of Animal Cells: A Manual of Basic Technique.* 2nd ed. A. R. Liss, New York and in U.S. Pat. Nos. 6,176,089; 6,140,123; 5,629,145; and 4,455,842; among other places.

V. Transgenic Animals

The present invention also provides a transgenic animal comprising a disruption of T2R76 gene expression and optionally another T2R disruptor. Altered gene expression can include expression of an altered level or mutated variant of a T2R76 gene. The present invention provides nucleic acids encoding T2R76 that can be used to prepare constructs for generating a transgenic animal. Also provided is genomic localization data useful for preparation of constructs targeted to the T2R 76 locus.

In one embodiment of the present invention, the transgenic animal can comprise a mouse with targeted modification of the mouse T2R76 locus and can further comprise mice strains with complete or partial functional inactivation of the T2R76 genes in all somatic cells.

In an alternative embodiment, a transgenic animal in accordance with the present invention is prepared using anti-sense or ribozyme T2R76 constructs, driven by a universal or tissue-specific promoter, to reduce levels of T2R76 gene expression in somatic cells, thus achieving a "knock-down" phenotype. The present invention also provides the generation of murine strains with conditional or inducible inactivation of T2R 76. Such murine strains can also comprise additional synthetic or naturally occurring mutations, for example a mutation in any other T2R gene.

The present invention also provides mice strains with specific "knocked-in" modifications in the T2R76 gene, for example to create an over-expression or dominant negative phenotype. Thus, "knocked-in" modifications include the expression of both wild type and mutated forms of a nucleic acid encoding a T2R76 polypeptide.

Techniques for the preparation of transgenic animals are known in the art. Exemplary techniques are described in U.S. Pat. No. 5,489,742 (transgenic rats); U.S. Pat. Nos. 4,736, 866, 5,550,316, 5,614,396, 5,625,125 and 5,648,061 (transgenic mice); U.S. Pat. No. 5,573,933 (transgenic pigs); U.S. Pat. No. 5,162,215 (transgenic avian species) and U.S. Pat. No. 5,741,957 (transgenic bovine species), the entire contents of each of which are herein incorporated by reference.

For example, a transgenic animal of the present invention can comprise a mouse with a targeted modification of the mouse T2R76. Mice strains with complete or partial functional inactivation of the T2R76 gene in all somatic cells can be generated using standard techniques of site-specific recombination in murine embryonic stem cells. See Capecchi (1989) *Science* 244:1288-1292; Thomas & Capecchi (1990) *Nature* 346:847-850; and Delpire et al. (1999) *Nat Genet* 22:192195.

VI. T2R76 Antibodies

In another aspect of the invention, a method is provided for producing an antibody that specifically binds a T2R76 polypeptide. According to the method, a full-length recombinant T2R76 polypeptide is formulated so that it can be used as an effective immunogen, and used to immunize an animal so as to generate an immune response in the animal. The immune response is characterized by the production of antibodies that can be collected from the blood serum of the animal. The present invention also provides antibodies produced by methods that employ the novel T2R76 polypeptides disclosed herein, including SEQ ID NO:2.

The term "antibody" refers to an immunoglobulin protein, or functional portion thereof, including a polyclonal antibody, a monoclonal antibody, a chimeric antibody, a hybrid antibody, a single chain antibody, a mutagenized antibody, a humanized antibody, and antibody fragments that comprise an antigen binding site (e.g., Fab and Fv antibody fragments). In a preferred embodiment of the invention, a T2R76 antibody comprises a monoclonal antibody. Thus, the present invention also encompasses antibodies and cell lines that produce monoclonal antibodies as described herein.

The term "specifically binds", when used to describe binding of an antibody to a T2R76 polypeptide, refers to binding to a T2R76 polypeptide in a heterogeneous mixture of other polypeptides.

The phrases "substantially lack binding" or "substantially no binding", as used herein to describe binding of an antibody to a control polypeptide or sample, refers to a level of binding that encompasses non-specific or background binding, but does not include specific binding.

Techniques for preparing and characterizing antibodies are known in the art. See e.g., Harlow & Lane (1988) *Antibodies: A Laboratory Manual*, Cold Spring Harbor Laboratory Press, Cold Spring Harbor, N.Y. and U.S. Pat. Nos. 4,196,265; 4,946,778; 5,091,513; 5,132,405; 5,260,203; 5,677,427; 5,892,019; 5,985,279; and 6,054,561.

T2R76 antibodies prepared as disclosed herein can be used in methods known in the art relating to the localization and activity of T2R76 polypeptides, e.g., for cloning of nucleic acids encoding a T2R76 polypeptide, immunopurification of a T2R76 polypeptide, imaging a T2R76 polypeptide in a biological sample, and measuring levels of a T2R76 polypeptide in appropriate biological samples. To perform such methods, an antibody of the present invention can further comprise a detectable label, including but not limited to a radioactive label, a fluorescent label, an epitope label, and a label that can be detected in vivo. Methods for selection of a label suitable for a particular detection technique, and methods for conjugating to or otherwise associating a detectable label with an antibody are known to one skilled in the art.

VIII. T2R76 Modulators

The present invention further discloses assays to identify modulators of T2R76 activity. An assay can employ a system for expression of a T2R76 polypeptide, as disclosed herein above, or an isolated T2R76 polypeptide produced in such a system wherein such T2R polypeptide may be expressed with other T2R polypeptides. The present invention also provides modulators of T2R76 activity identified using the disclosed methods.

The term "modulate" means an increase, decrease, or other alteration of any or all chemical and biological activities or properties of a T2R76 polypeptide. Thus, the method for identifying modulators involves assaying a level or quality of T2R76 function.

A method for identifying a modulator of T2R76 function can comprise: (a) providing a recombinant expression system whereby a T2R76 polypeptide is expressed in a host cell, and wherein the T2R76 polypeptide comprises a T2R76 polypeptide; (b) providing a test substance to the system of (a); (c) assaying the level or quality of T2R76 function in the presence of the test substance; (d) comparing the level or quality of T2R76 function in the presence of the test substance with a control level or quality of T2R76 function; and (e) identifying a test substance as a T2R76 modulator by determining a level or quality of T2R76 function in the presence of the test substance as significantly changed when compared to a control level or quality of T2R76 function. In some embodiments, the expression system will also provide for T2R76 to be co-expressed with at least one other T2R.

A control level or quality of T2R76 activity refers to a level or quality of wild type T2R76 activity. Preferably, a system for recombinant expression of a T2R76 polypeptide comprises SEQ ID NO:2. When evaluating the modulating capacity of a test substance, a control level or quality of T2R76 activity comprises a level or quality of activity in the absence of a test substance.

The term "significantly changed", as used herein to refer to an altered level or activity of a T2R polypeptide, e.g., T2R76 polypeptide, and refers to a quantified change in a measurable quality that is larger than the margin of error inherent in the measurement technique, preferably an increase or decrease by about 2-fold or greater relative to a control measurement, more preferably an increase or decrease by about 5-fold or greater, and most preferably an increase or decrease by about 10-fold or greater.

In one embodiment of the invention, assaying T2R76 function comprises determining a level of T2R76 gene expression.

In another embodiment of the invention, assaying T2R76 function comprises assaying binding activity of a recombinantly expressed T2R76 polypeptide. For example, a T2R76 activity can comprise an amount or a strength of binding of a modulator to a T2R76 polypeptide.

In still another embodiment of the invention, assaying T2R76 function can comprise assaying an active conformation of a T2R76 polypeptide.

In a preferred embodiment of the invention, assaying T2R76 function comprises assaying activation of intracellular signaling events in response to binding of a ligand or a modulator to a T2R76 polypeptide. For example, ligand-mediated stimulation of G protein exchange activity can be assayed by measuring an amount of binding of [$^{35}$S]GTPγS to a T2R76 polypeptide, as described further herein below and in Example 3.

Modulators identified by the disclosed methods can comprise agonists and antagonists. As used herein, the term "agonist" means a substance that activates, synergizes, or potentiates the biological activity of a T2R76 polypeptide. As used herein, the term "antagonist" refers to a substance that blocks or mitigates the biological activity of a T2R76 polypeptide. A modulator can also comprise a ligand or a substance that specifically binds to a T2R76 polypeptide. Activity and binding assays for the determination of a T2R76 modulator can be performed in vitro or in vivo.

In one embodiment of the invention, such assays are useful for the identification of T2R76 modulators that can be developed as additives to alter taste of a composition for oral use, including but not limited to food, beverages, oral washes, dentifrices, cosmetics, and pharmaceuticals, as described further herein below under the heading "Applications." For example, an inhibitor of T2R76 can be used to reduce bitter taste.

In another embodiment of the invention, such assays are useful for the identification of T2R76 modulators that can be developed as additives to alter taste of a compound that is of possible but undesirable oral use, for example household cleansers, poisons, etc. Thus, an agonist of T2R76 can be used to introduce or increase bitter taste of a composition to thereby discourage its oral use.

In still another embodiment of the invention, assays using a recombinant T2R76 polypeptide can be performed for the purpose of prescreening bioactive agents, wherein an interaction between the agent and T2R76 is undesirable. For example, a drug intended for administration to a subject can be tested for T2R76 modulating activity that can result in an undesirable bitter taste.

In still another embodiment of the invention, an assay disclosed herein can be used to characterize a mutant T2R76 polypeptide, for example a mutant polypeptide that is linked to a differences in bitter taste perception. Recombinant expression of mutated T2R76 polypeptides will permit further analysis of disorder-related T2R76 polypeptides.

In accordance with the present invention there is also provided a rapid and high throughput screening method that relies on the methods described herein. This screening method comprises separately contacting a T2R76 polypeptide with a plurality of test substances. In such a screening method the plurality of target substances preferably comprises more than about 104 samples, or more preferably comprises more than about 105 samples, and still more preferably more than about 106 samples.

The in vitro and cellular assays of the invention can comprise soluble assays, or can further comprise a solid phase substrate for immobilizing one or more components of the assay. For example, a T2R76 polypeptide, or a cell expressing a T2R76 polypeptide, and optionally another T2R polypeptide can be bound directly to a solid state component via a covalent or non-covalent linkage. Further, optionally, the binding can include a linker molecule or tag that mediates indirect binding of a T2R76 polypeptide to a substrate.

Representative linkers include known binding pairs (e.g., biotin and avidin), antibodies that recognize known antigens, synthetic polymers (e.g., polyurethanes, polyesters, polycarbonates, polyureas, polyamides, polyethyleneimines, polyarylene sulfides, polysiloxanes, polyimides, and polyacetates), peptides, ethers. A linker can optionally comprise a flexible linker, for example ploy (ethelyne glycol) linkers (available from Shearwater Polymers, Inc. of Huntsville, Ala., United States of America). Optionally, a linker can further comprise amide, sulfhydryl, or heterofunctional binding sites.

Linkers can be affixed to a solid substrate using any of a variety of current methods, including derivatization of a substrate whereby it reacts with a linker or non-chemical approaches that employ heat or ultraviolet cross-linking. Representative protocols can be found, for example, in Merrifield (1963) *J Am Chem Soc* 85:2149-2154 (describing solid phase synthesis of, e.g., peptides); Geysen et al. (11987) *J Immun Meth* 102:259-274 (describing synthesis of solid phase components on pins); Frank & boring (1988) *Tetrahedron* 44:60316040 (describing synthesis of various peptide sequences on cellulose disks); Fodor et al. (1991) *Science* 251:767-777; and Kozal et al. (1996) *Nat Med* 2(7):753759 (describing arrays of biopolymers fixed to solid substrates), Merrifield (1963) *J Am Chem Soc* 85:2149-2154 (describing solid phase synthesis of, e.g., peptides); Geysen et al. (1987) *J Immun Meth* 102:259-274 (describing synthesis of solid phase components on pins); Frank & Doring (1988) *Tetrahedron* 44:60316040 (describing synthesis of various peptide sequences on cellulose disks); Fodor et al. (1991) *Science* 251:767-777; and Kozal et al. (1996) *Nat Med* 2(7):753759 (describing arrays of biopolymers fixed to solid substrates), among other places.

VII.A. Test Substances

A potential modulator assayed using the methods of the present invention comprises a candidate substance. As used herein, the terms "candidate substance" and "test substance" are used interchangeably, and each refers to a substance that is suspected to interact with a T2R76 polypeptide, including any synthetic, recombinant, or natural product or composition. A test substance suspected to interact with a polypeptide can be evaluated for such an interaction using the methods disclosed herein.

Representative test substances include but are not limited to peptides, oligomers, nucleic acids (e.g., aptamers), small molecules (e.g., chemical compounds), antibodies or fragments thereof, nucleic acid-protein fusions, any other affinity agent, and combinations thereof. A test substance can additionally comprise a carbohydrate, a vitamin or derivative thereof, a hormone, a neurotransmitter, a virus or receptor binding domain thereof, an ops or rhodopsin, an odorant, a pheromone, a toxin, a growth factor, a platelet activation factor, a neuroactive peptide, or a neurohormone. Preferably, a candidate substance elicits bitter taste perception. A candidate substance to be tested can be a purified molecule, a homogenous sample, or a mixture of molecules or compounds.

The term "small molecule" as used herein refers to a compound, for example an organic compound, with a molecular weight of less than about 1,000 daltons, more preferably less than about 750 daltons, still more preferably less than about 600 daltons, and still more preferably less than about 500 daltons. A small molecule also preferably has a computed log octanol-water partition coefficient in the range of about −4 to about +14, more preferably in the range of about −2 to about +7.5.

Test substances can be obtained or prepared as a library. As used herein, the term "library" means a collection of molecules. A library can contain a few or a large number of different molecules, varying from about ten molecules to several billion molecules or more. A molecule can comprise a naturally occurring molecule, a recombinant molecule, or a synthetic molecule. A plurality of test substances in a library can be assayed simultaneously. Optionally, test substances derived from different libraries can be pooled for simultaneous evaluation.

Representative libraries include but are not limited to a peptide library (U.S. Pat. Nos. 6,156,511, 6,107,059, 5,922, 545, and 5,223,409), an oligomer library (U.S. Pat. Nos. 5,650,489 and 5,858,670), an aptamer library (U.S. Pat. Nos. 6,180,348 and 5,756,291), a small molecule library (U.S. Pat. Nos. 6,168,912 and 5,738,996), a library of antibodies or antibody fragments (U.S. Pat. Nos. 6,174,708, 6,057,098, 5,922,254, 5,840,479, 5,780,225, 5,702,892, and 5,667,988), a library of nucleic acid-protein fusions (U.S. Pat. No. 6,214,553), and a library of any other affinity agent that can potentially bind to a T2R76 polypeptide (e.g., U.S. Pat. Nos. 5,948,635, 5,747,334, and 5,498,538).

A library can comprise a random collection of molecules. Alternatively, a library can comprise a collection of molecules having a bias for a particular sequence, structure, or conformation. See e.g., U.S. Pat. Nos. 5,264,563 and 5,824, 483. Methods for preparing libraries containing diverse populations of various types of molecules are known in the art, for example as described in U.S. patents cited herein above. Numerous libraries are also commercially available.

VII.B. Binding Assays

In another embodiment of the invention, a method for identifying of a T2R76 modulator comprises determining specific binding of a test substance to a T2R76 polypeptide or a heteromenic receptor comprising a T2R76 polypeptide and one or more other T2R polypeptides. The term "binding" refers to an affinity between two molecules. Preferably, specific binding also encompasses a quality or state of mutual action such that an activity of one protein or compound on another protein is inhibitory (in the case of an inhibitor or antagonist) or enhancing (in the case of an activator or agonist).

The phrase "specifically (or selectively) binds", when referring to the binding capacity of a candidate modulator, refers to a binding reaction which is determinative of the presence of the protein in a heterogeneous population of proteins and other biological materials. The binding of a modulator to a T2R76 polypeptide can be considered specific if the binding affinity is about $1 \times 10^4 M^{-1}$ to about $1 \times 10^6 M^{-1}$ or greater. The phrase "specifically binds" also refers to saturable binding. To demonstrate saturable binding of a test substance to a T2R76 polypeptide, Scatchard analysis can be carried out as described, for example, by Mak et al. (1989) J Biol Chem 264:21613-21618.

The phases "substantially lack binding" or "substantially no binding", as used herein to describe binding of a modulator to a control polypeptide or sample, refers to a level of binding that encompasses non-specific or background binding, but does not include specific binding.

Several techniques can be used to detect interactions between a T2R76 polypeptide and a test substance without employing a known competitive modulator. Representative methods include, but are not limited to, Fluorescence Correlation Spectroscopy, Surface-Enhanced Laser Desorption/Ionization Time-Of-flight Spectroscopy, and Biacore technology, each technique described herein below. These methods are amenable to automated, high-throughput screening.

Fluorescence Correlation Spectroscopy (FCS) measures the average diffusion rate of a fluorescent molecule within a small sample volume (Tallgren, 1980). The sample size can be as low as 103 fluorescent molecules and the sample volume as low as the cytoplasm of a single bacterium. The diffusion rate is a function of the mass of the molecule and decreases as the mass increases. FCS can therefore be applied to polypeptide-ligand interaction analysis by measuring the change in mass and therefore in diffusion rate of a molecule upon binding. In a typical experiment, the target to be analyzed (e.g., a T2R76 polypeptide) is expressed as a recombinant polypeptide with a sequence tag, such as a poly-histidine sequence, inserted at the N-terminus or C-terminus. The expression is mediated in a host cell, such as *E. coli*, yeast, *Xenopus oocytes*, or mammalian cells. The polypeptide is purified using chromatographic methods. For example, the poly-histidine tag can be used to bind the expressed polypeptide to a metal chelate column such as $Ni^{2+}$ chelated on iminodiacetic acid agarose. The polypeptide is then labeled with a fluorescent tag such as carboxytetramethylrhoda mine or BODIPYTm reagent (available from Molecular Probes of Eugene, Oreg.). The polypeptide is then exposed in solution to the potential ligand, and its diffusion rate is determined by FCS using instrumentation available from Carl Zeiss, Inc. (Thornwood, N.Y.). Ligand binding is determined by changes in the diffusion rate of the polypeptide.

Surface-Enhanced Laser Desorption/Ionization (SELDI) was developed by Hutchens & Yip (1993) *Rapid Commun Mass Spectrom* 7:576-580.When coupled to a time-of-flight mass spectrometer (TOF), SELDI provides a technique to rapidly analyze molecules retained on a chip. It can be applied to ligand-protein interaction analysis by covalently binding the target protein, or portion thereof, on the chip and analyzing by mass spectrometry the small molecules that bind to this protein (Worrall et al., 1998). In a typical experiment, a target polypeptide (e.g., a T2R76 polypeptide) is recombinantly expressed and purified. The target polypeptide is bound to a SELDI chip either by utilizing a poly-histidine tag or by other interaction such as ion exchange or hydrophobic interaction. A chip thus prepared is then exposed to the potential ligand via, for example, a delivery system able to pipet the ligands in a sequential manner (autosampler). The chip is then washed in solutions of increasing stringency, for example a series of washes with buffer solutions containing an increasing ionic strength. After each wash, the bound material is analyzed by submitting the chip to SELDI-TOF. Ligands that specifically bind a target polypeptide are identified by the stringency of the w6sh needed to elute them.

Biacore relies on changes in the refractive index at the surface layer upon binding of a ligand to a target polypeptide (e.g., a T2R76 polypeptide) immobilized on the layer. In this system, a collection of small ligands is injected sequentially in a 2-5 microliter cell, wherein the target polypeptide is immobilized within the cell. Binding is detected by surface plasmon resonance (SPR) by recording laser light refracting from the surface. In general, the refractive index change for a given change of mass concentration at the surface layer is practically the same for all proteins and peptides, allowing a single method to be applicable for any protein (Liedberg et al., 1983. In a typical experiment, a target protein is recombinantly expressed, purified, and bound to a Biacore chip. Binding can be facilitated by utilizing a poly-histidine tag or by other interaction such as ion exchange* or hydrophobic interaction. A chip thus prepared is then exposed to one or more potential ligands via the delivery system incorporated in the instruments sold by Biacore (Uppsala, Sweden) to pipet the ligands in a sequential manner (autosampler). The SPR signal on the chip is recorded and changes in the refractive index indicate an interaction between the immobilized target and the ligand. Analysis of the signal kinetics of on rate and off rate allows the discrimination between non-specific and specific interaction. See also Homola et al. (1999) *Sensors and Actuators* 54:3-15 and references therein.

VII.C. Conformational Assay

The present invention also provides a method for identifying a T2R76 modulator that relies on a conformational change of a T2R76 polypeptide expressed alone or in association with another T2R polypeptide when bound by or otherwise interacting with a T2R76 modulator.

Application of circular dichroism to solutions of macromolecules reveals the conformational states of these macromolecules. The technique can distinguish random coil, alpha helix, and beta chain conformational states.

To identify modulators of a T2R76 polypeptide, circular dichroism analysis can be performed using a recombinantly expressed T2R76 polypeptide. A T2R76 polypeptide is purified, for example by ion exchange and size exclusion chromatography, and mixed with a test substance. The mixture is subjected to circular dichroism. The conformation of a T2R76 polypeptide in the presence of a test substance is compared to a conformation of a T2R76 polypeptide in the absence of a test substance. A change in conformational state of a T2R76 polypeptide in the presence of a test substance can thus be used to identify a T2R76 modulator. Representative methods are described in U.S. Pat. Nos. 5,776,859 and 5,780, 242. The T2R76 polypeptide may be comprised in a heteromenic receptor comprising another T2R polypeptide.

VII.D. Receptor Activation Assays

In a preferred embodiment of the invention, a method for identifying a T2R76 modulator employs a functional T2R76 polypeptide. Novel T2R76 polypeptides disclosed herein include SEQ ID NO:2. Representative methods for determining T2R76 function include assaying ligand-mediated activation of intracellular signaling events, as described herein below.

The effect of a test substance on T2R76 function can comprise assaying any physiological change elicited by T2R76 activity, including but not limited to phosphorylation of a T2R76 polypeptide, G protein binding to a T2R76 polypeptide, ion flux in a cell expressing a T2R76 polypeptide, changes in gene transcription, changes in cell metabolism (e.g., cell growth), changes in intracellular second messengers (e.g., $Ca^{2+}$, IP3, cGMP, cAMP), and changes in transmitter or hormone release. GPCR signal transduction and methods for assaying the same are described in *Methods in Enzymology* volumes 237 and 238 (1994). See also Berridge & Irvine (1984) *Nature* 312:315-321; Bourne et al. (1991) *Nature* 10:349:117-27; Bourne et al. (1990) *Nature* 348:125-32; Felley-Bosco et al. (1994) *Am J Resp Cell and Mol Biol* 11:159-164; Mistili & Spector (1997) *Nat Biotech* 15:961-964; Offermanns & Simon (1995) *J Biol Chem* 270:15175-15180; Pitcher et al. (1998) *Annu Rev Biochem* 67:653-92; and U.S. Pat. Nos. 4,115,538; 5,436,128; 6,004,808, 6,403, 305, and 6,255,059.

In a preferred embodiment of the invention, assaying T2R76 function comprises assaying coupling of a recombinantly expressed T2R76 polypeptide alone or in association with another T2R polypeptide to gustducin or a promiscuous G protein such as Gq or transducin. A representative level of T2R76 activity can thus comprise an amount exchange of GDP for GTPγS on gustducin as described in Example 3. A representative quality of T2R76 activity can comprise, for example, the selective activation of G protein a subunits.

In accordance with the method, cells expressing T2R76 can be provided in the form of a kit useful for performing an assay of T2R76 function. Thus, cells can be frozen as described herein above and transported while frozen to others for performance of an assay. For example, in one embodiment of the invention, a test kit is provided for detecting a T2R76 modulator, the kit comprising: (a) frozen cells transfected with DNA encoding a full-length T2R76 polypeptide; and (b) a medium for growing the cells.

Preferably, a cell used in such an assay comprises a cell that is substantially devoid of native T2R76 and polypeptides substantially similar to T2R76. A preferred cell comprises a eukaryotic cell, for example a HEK-293 cell.

The term "substantially devoid of", as used herein to describe a host cell or a control cell, refers to a quality of having a level of native T2R76, a level of a polypeptide substantially similar to T2R76, or a level of activity thereof, comprising a background level. The term "background level" encompasses non-specific measurements of expression or activity that are typically detected in a cell free of T2R76 and free of polypeptides substantially similar to a T2R76 polypeptide.

Cells used in the assays of the invention preferably comprise a functional G protein that is capable of coupling a T2R76 receptor to an intracellular signaling pathway. In one embodiment of the invention, the functional G protein can comprise a G protein that displays promiscuous coupling, for example Gα15 and Gα16. See Wilkie et al. (1991) *Proc And Acad Sci USA* 88:10049-10053 and U.S. Pat. No. 6,004,808.

Also preferably, all assays employing cells expressing recombinant T2R76 additionally employ control cells that are substantially devoid of native T2R76 and polypeptides substantially similar to a T2R76 polypeptide. When using transiently transfected cells, a control cell can comprise, for example, an untransfected host cell. When using a stable cell line expressing a T2R76 polypeptide, a control cell can comprise, for example, a parent cell line used to derive the T2R76-expressing cell line.

Assays of T2R76 activity that employ transiently transfected cells preferably include a marker that distinguishes transfected cells from non-transfected cells. The term "marker" refers to any detectable molecule that can be used to distinguish a cell that recombinantly expresses T2R76 from a cell that does not recombinantly express a T2R76 polypeptide. Preferably, a marker is encoded by or otherwise associated with a construct for T2R76 expression, such that cells are simultaneously transfected with a nucleic acid molecule encoding T2R76 and the marker. Representative detectable molecules that are useful as markers include but are not limited to a heterologous nucleic acid, a polypeptide encoded by a transfected construct (e.g., an enzyme or a fluorescent polypeptide), a binding protein, and an antigen. For example, a maker can comprise a rhodopson tag, which can be detected immunologically, as described in Example 2.

Examples of enzymes that are useful as markers include phosphatases (such as acid or alkaline phosphatase), β-galactosidase, urease, glucose oxidase, carbonic anhydrase, acetylcholinesterase, glucoamylase, maleate dehydrogenase, glucose-6-phosphate dehydrogenase, β-glucosidase, proteases, pyruvate decarboxylase, esterases, luciferase, alcohol dehydrogenase, or peroxidases (such as horseradish peroxidase).

A marker comprising an enzyme can be detected based on activity of the enzyme. Thus, a substrate is be added to catalyze a reaction the end product of which is detectable, for example using s pectro photometer, a luminometer, or a fluorimeter. Substrates for reaction by the above-mentioned enzymes, and that produce a detectable reaction product, are known to one of skill in the art.

A preferred marker comprises an encoded polypeptide that can be detected in the absence of an added substrate. Representative polypeptides that can be detected directly include GFP and EGFP. Common research equipment has been developed to perform high-throughput detection of fluorescence, for example GFP or EGFP fluorescence, including instruments from GSI Lumonics (Watertown, Mass., United States of America), Amersharn Pharmacia Biotech/Molecular Dynamics (Sunnyvale, Calif., United States of America), Applied Precision Inc. (Issauah, Wash., United States of America), and Genomic Solutions Inc. (Ann Arbor, Mich., United States of America). Most of the commercial systems use some form of scanning technology with photomultiplier tube detection.

VII. E. Rational Design

The knowledge of the structure a native T2R76 polypeptide provides an approach for rational design of modulators and diagnostic agents. In brief, the structure of a T2R76 polypeptide can be determined by X-ray crystallography and/or by computational algorithms that generate three-dimensional representations. See Saqi et al. (1999) *Bioinformatics* 15:521-522; Huang et al. (2000) Pac Symp Biocomput:230-241; and PCT International Publication No. WO 99/26966. Alternatively, a working model of a T2R76 polypeptide structure can be derived by homology modeling (Maalouf et al., 1998). Computer models can further predict binding of a protein structure to various substrate molecules that can be synthesized and tested using the assays described herein above. Additional compound design techniques are described in U.S. Pat. Nos. 5,834,228 and 5,872,011.

In general, a T2R76 polypeptide is a membrane protein, and can be purified in soluble form using detergents or other suitable amphiphilic molecules. The resulting T2R76 polypeptide is in sufficient purity and concentration 'for crystallization. The purified T2R76 polypeptide preferably runs as a single band under reducing or non-reducing polyacrylamide gel electrophoresis (PAGE). The purified T2R76 polypeptide can be crystallized under varying conditions of at least one of the following: pH, buffer type, buffer concentration, salt type, polymer type, polymer concentration, other precipitating ligands, and concentration of purified T2R76. Methods for generating a crystalline polypeptide are known in the art and can be reasonably adapted for determination of a T2R76 polypeptide as disclosed herein. See e.g., Deisenhofer et al. (1984) *J Mol Biol* 180:385-398; Weiss et al. (1990) *FEBS* Lett 267:268-272; or the methods provided in a commercial kit, such as the CRYSTAL SCREEN™ kit (available from Hampton Research of Riverside, Calif., United States of America).

A crystallized T2R76 polypeptide can be tested for functional activity and differently sized and shaped crystals are further tested for suitability in X-ray diffraction. Generally, larger crystals provide better crystallography than smaller crystals, and thicker crystals provide better crystallography than thinner crystals. Preferably, T2R76 crystals range in size from 0.1-1.5 mm. These crystals diffract X-rays to at least 10 A resolution, such as 1.5-10.0 A or any range of value therein, such as 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5 or 3, with 3.5 A or less being preferred for the highest resolution.

VIII. Methods for Detecting a T2R76 Polypeptide

The present invention further provides methods for detecting a T2R76 polypeptide. The disclosed methods can be used for determining altered levels of T2R76 expression that are associated with T2R76-related differences in taste perception.

In one embodiment of the invention, the method involves performing an immunochemical reaction with an antibody that specifically recognizes a T2R76 polypeptide, wherein the antibody was prepared according to a method of the present invention for producing such an antibody. Thus, the method comprises: (a) obtaining a biological sample comprising peptidic material; (b) contacting the biological sample with an antibody that specifically binds a T2R76 polypeptide and that was produced according to the disclosed methods, wherein the antibody comprises a detectable label; and (c) detecting the detectable label, whereby a T2R76 polypeptide in a sample is detected.

Techniques for detecting such antibody-antigen conjugates or complexes are known in the art and include but are not limited to centrifugation, affinity chromatography and other immunochemical methods. See e.g., Manson (1992) *Immunochemical Protocols*. Humana Press, Totowa, N.J., United States of America; Ishikawa (1999) *Ultrasensitive and Rapid Enzyme Immunoassa* . Elsevier, Amsterdam/New York, United States of America; Law (1996) *Immunoassay: Practical Guide*. Taylor & Francis, London/Bristol, Pa., United States of America; Chan (1996) *Immunoassay Automation: An Updated Guide to Systems*. Academic Press, San Diego; Liddell & Weeks (1995) *Antibody Technology*. Bios Scientific Publishers, Oxford, United Kingdom; Masseyeff et al. (1993) *Methods of Immunological Analysis*. VCH Verlagsgesellschaft/VCH Publishers, Weinheim, Federal Republic of Germany/New York, United States of America; Walker & Rapley (1993) *Molecular and Antibody Probes in Diagnosis*. Wiley, Chichester, N.Y.; Wyckoff et al. (1985) *Diffraction Methods for Biological Macromolecules*. Academic Press, Orlando, Fla., United States of America; and references cited therein.

In another embodiment of the invention, a modulator that shows specific binding to a T2R76 polypeptide is used to detect a T2R76 polypeptide. Analogous to detection of a T2R76 polypeptide using an antibody, the method comprises: (a) obtaining a biological sample comprising peptidic material; (b) contacting the biological sample with a modulator of a T2R76 polypeptide, wherein the modulator comprises a detectable label; and (c) detecting the detectable label, whereby a T2R76 polypeptide in a sample is detected. Any suitable detectable label can be used, for example a fluorophore or epitope label.

IX. Applications

The present invention provides methods for identification of modulators of a T2R76 polypeptide. The modulators of the invention are useful for altering bitter taste perception, for example to suppress or enhance bitter taste perception.

IX.A. Subjects

The term "subject" as used herein includes any vertebrate species, preferably warm-blooded vertebrates such as mammals and birds. More particularly, the methods of the present invention are contemplated for the treatment of tumors in mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants and livestock (such as cattle, oxen, sheep, giraffes, deer, goats, bison, and camels), and horses. Also contemplated is the treatment of birds, including those kinds of birds that are endangered or kept in zoos, as well as fowl, and more particularly domesticated fowl or poultry, such as turkeys, chickens, ducks, geese, guinea fowl, and the like, as they are also of economical importance to humans.

IX.B. Compositions

In accordance with the methods of the present invention, a composition that is administered to alter taste perception in a subject comprises an effective amount of a T2R76 modulator. A T2R76 modulator can comprise any one of the types of test substances described herein above. T2R76 modulators identified as disclosed herein can be used to prepare a composition for oral use, including but not limited to food, beverages, oral washes, dentifrices, cosmetics, and pharmaceuticals, for example any of those compound listed herein below. T2R76 modulators can also be used as additives to alter the taste of a compound that is of possible but undesirable oral use, for example household cleansers, poisons, etc.

Representative foods having an undesirable or bitter taste include, but are not limited to, citrus fruits such as grapefruit, orange, and lemon; vegetables such as tomato, pimento, celery, melon, carrot, potato, and asparagus; seasoning or flavoring materials such as flavor, sauces, soy sauce, and red pepper; foods originating from soybean; emulsion foods such as cream, dressing, mayonnaise, and margarine; processed marine products such as fish meat, ground fish meat, and fish eggs; nuts such as peanuts; fermented foods such as fermented soybean; meats and processed meats; pickles; noodles; soups including powdery soups; dairy products such as cheese; breads and cakes; confectioneries such as candies, chewing gum, and chocolate; and specifically prepared foods for health.

Representative cosmetics eliciting bitter taste (e.g., skin lotions, creams, face packs, lip sticks, foundations, shaving preparations, after-shave lotions, cleansing foams, and cleansing gels) include but are not limited to those compositions that include surfactants such as sodium alkyl sulfate and sodium monoalkyl phosphate; fragrances such as menthol, linalool, phenylethyl alcohol, ethyl propionate, geraniol, linalyl acetate and benzyl acetate; antimicrobials such as methyl paraben, propyl paraben and butyl paraben; humectants such as lactic acid and sodium lactate; alcohol-denaturating agents such as sucrose octaacetate and brucine; and astringents such as aluminum lactate.

Representative pharmaceuticals having a bitter taste include acetaminophen, terfenadine, guaifenesin, trimethoprim, prednisolone, ibuprofen, prednisolone sodium phosphate, methacholine, neostigmine, epinephrine, albuterol, pseudoephedrine hydrochloride, diphenhydramine, chlorpheniramine maleate, phenothiazine, chlorpromazine, ch lord iazepoxide, amitriptyline, barbiturates, diphenylhydantoin, caffeine, morphine, demerol, codeine, lomotil, lidocaine, salicylic acid, sulfonamides, chloroquine, a vitamin preparation, minerals and penicillins.

The modulators can also be administered as part of prepared food, beverage, oral wash, dentifrice, cosmetic, or drug. To prepare a composition for administration to a subject, a T2R76 modulator can be admixed with a compound whose taste is to be modulated in amount comprising about 0.001% to about 10% by weight, preferably from about 0.01% to about 8% by weight, more preferably from about 0.1% to about 5% by weight, and most preferably from about 0.5% to about 2% by weight.

Suitable formulations include solutions, extracts, elixirs, spirits, syrups, suspensions, powders, granules, capsules, pellets, tablets, and aerosols. Optionally, a formulation can include a pharmaceutically acceptable carrier, a suspending agent, a solubilizer, a thickening agent, a stabilizer, a preservative, a flavor, a colorant, a sweetener, a perfume, or a combination thereof. T2R76 modulators and compositions can be presented in unit-dose or multi-dose sealed containers, such as ampules and vials.

IX.C. Administration

T2R76 modulators can be administered directly to a subject for modulation of taste perception. Preferably, a modulator of the invention is administered orally or nasally.

In accordance with the methods of the present invention, an effective amount of a T2R76 modulator is administered to a subject. The term "effective amount" refers to an amount of a composition sufficient to modulate T2R76 activation and/or to modulate bitter taste perception.

An effective amount can be varied so as to administer an amount of an T2R76 modulator that is effective to achieve the desired taste perception. The selected dosage level will depend upon a variety of factors including the activity of the T2R76 modulator, formulation, combination with other compositions (e.g., food, drugs, etc.), the intended use (e.g., as a food additive, dentifrice, etc.), and the physical condition and prior medical history of the subject being treated.

An effective amount or dose can be readily determined using in vivo assays of taste perception as are known in the art. Representative methods for assaying taste perception are described in Example 4.

EXAMPLES

The following Examples have been included to illustrate modes of the invention. Certain aspects of the following Examples are described in terms of techniques and procedures found or contemplated by the present co-inventors to work well in the practice of the invention. These Examples illustrate standard laboratory practices of the co-inventors. In light of the present disclosure and the general level of skill in the art, those of skill will appreciate that the following Examples are intended to be exemplary only and that. numerous changes, modifications, and alterations can be employed without departing from the scope of the invention.

Example 1

Cloning of Human T2R76

A novel gene encoding a human bitter taste receptor was identified in the human genome sequence databases. Novel hT2R member, hT2R76 is located on human chromosome 7. The chromosomal location of T2R76 DNA sequence was determined by screening the University of California (Santa Cruz, Calif.) Genomics web site. This analysis showed that T2R76 is located on chromosome 7 in the region 144062692-144063648. The bitter taste of certain compounds, such as phenylthiocarbarnate, have been linkage genetically to chromosomes 5 and 7. (Guo et al. (2001) *Ann Hum Biol* 28:111-42). Thus, T2R76 is predicted to be involved in binding and recognition of certain bitter tastants.

Human T2R76 was initially identified by reiterated sequence search of DNA sequence databases with previously described hT2R sequences. A full-length open reading frame encoding hT2R76 was then isolated by PCR amplification of genomic DNA. The amino acid sequence of hT2R76 was derived by conceptual translation of the corresponding open reading frame. The hT2R76 nucleotide and amino acid sequences are set forth as SEQ ID NO:1 and SEQ ID NO:2, respectively.

The intronless open reading frame of hT2R76 encodes a putative receptor protein 318 amino acid residues in length. A comparison of the hT2R76 protein sequence with all known proteins in the public sequence databases using the BLASTP algorithm revealed its strong homology to the members of the mammalian bitter receptor family.

Example 2

Construction of rhod-hT2R76

A bridge overlap PCR extension technique was used to generate rhod-hT2R76 chimeras, which contain the first 38 amino acids of bovine *rhodopsin* in frame with human T2R76 coding sequences as described Chandrashekar et al. (2000) *Cell* 100:703-711. The chimeric rhod-hT2R76 gene was then cloned into the pFastBac-1 vector, and baculoviruses containing rhodopsin-tagged hT2R76 was produced using Bac-to-Bac system (Invitrogen Corporation of Carlsbad, Calif., United States of America). Expression of hT2R76 was confirmed by immunoblotting using anti-rhodopsin tag antibodies (136-30). Sf9 cells infected with hT2R76encoding baculovirus produced a protein of the expected molecular weight (~35 kDa).

Example 3

In Vitro G Protein Coupling of T2R76

An infectious bacmid encoding rhod-hT2R76 is prepared as described in Example 2. Insect larval cells are infected for 60 hours with recombinant bacmid and membranes are prepared as described by Ryba & Trindelli (1995) *J Biol Chem* 270:6757-6767. Peripheral proteins are removed by treatment with 5M urea and membranes are resuspended in 1 OmM HEPES pH 7.5, 1 mM EDTA, and 1 mM DTT. The expression of rhod-hT2R76 can be assessed by Western blotting using monocolonal antibody B6-30.

G proteins are isolated, for example as described by Hoon et al. (1995) *Cell* 96 629-636 and by Ryba & Trindelli (1995) *J Biol Chem* 270:6757-6767. Receptor-catalyzed exchange of GDP for GTPγS on gustducin is measured in the presence of 10 nM rhod-hT2R76, 100 μtM GDP, and 20 μM Gβ1γ8. GDP-GTPγS exchange on promiscuous G proteins (e.g., Gα5 or transducin) is performed as described in U.S. patent application Ser. No. 60/372,089. Measurements made at about 15-60 minute time points reflect the initial rate of GTPγS binding.

Example 4

Taste Study

A flavor acceptance study is conducted using a test composition comprising a T2R76 modulator identified as disclosed herein. A control composition lacking the T2R76 modulator, but which is otherwise substantially similar or identical to the test composition, is also used. The study employs a two-way crossover design, with all subjects evaluating both compositions, which are administered in one or more same amounts or doses. The test and control compositions are evaluated on a single study day. The sequence for administering the test and control compositions is randomized among subjects. All enrolled subjects complete all aspects of the study protocol. Subjects respond to each of the test and control compositions using ordinal taste scores (e.g., 1=very bitter, 2=bitter, 3=indifferent, 4=not that bitter, 5=not bitter at all). Adverse events are recorded. Effectiveness of a T2R76 modulator is determined by measuring a significant difference in palatability of the test composition when compared to the control composition.

Example 5

Response of hT2R76 to Bitter Compounds

A GTPγS binding assay is effected using a mammalian cell line (HEK293) that expresses hT2R76 as well as a control cell line that expresses a different hT2R (hT2R64). These cell lines are contacted with bitter compounds including 6-n-propylthiouracil (PROP), sucrose octaacetate, raffinose undacaacetate, (RUA), copper glycinate, denatonium and quinine at different concentrations ranging from 0.5 to 2 mm. The results of this assay are used to confirm that hT2R76 is a bitter taste receptor that is specifically activated by known bitter taste stimuli. In this GTPγS binding assay activity is determined either in the presence or absence of specific concentrations of known bitter compounds.

Example 6

High Throughput Screening Assay

Using the GTPγS binding assay, a library of over 15,000 compounds is screened to identify other compounds that specifically activate hT2R76. The structure of the specific compounds that activate hT276 in this assay are compared in order to predict compounds having similar structure that potentially will activate hT2R76. Libraries of compounds having these similar structures are then evaluated at different concentrations in the same GTPγS binding assay to identify other compounds that activate hT2R76.

Example 7

Human Taste Test

The compounds which activate hT2R76 in GTPγS binding assays are evaluated in human taste tests. These human taste tests are performed in consenting adults who are orally administered the identified compound at the concentration at which they activate hT2R76 in vitro. In these taste tests an identified compound (which activates hT2R76) is dissolved in water to achieve a compound concentration that activates hT2R76 in the in vitro GTPγS binding assay.

In this taste test, a sample of at least 5 persons taste a series of aqueous solutions containing a bitter compound. (In the preferred example, the bitter compound is a T2R76 agonist). Each of the persons ranks the degree of bitterness in a labeled magnitude scale ranging from 0 to 100 (0 is "barely detectable." and 100 is "strongest imaginable"). Next, each person tastes a series of aqueous solutions containing the bitter compound and the T2R76 inhibitor and ranks the degree of bitterness for each sample. The effectiveness of the T2R76 inhibitor is measured by the reduction in the degree of bitterness. As a means of comparison, a known bitter compound (quinine sulfate) is also tested and evaluated by each subject. The result of the taste tests are represented as the average rating in all subjects.

Example 8

Response of hT2R76 to Known Bitter Compounds

The results of this assay are used to identify bitter cmopounds that activate hT2R76. Based thereon, assays can be developed that identify compounds that block the activation of hT2R76 by such bitter compounds.

CONCLUSION

The results of these assays will provide a demonstration that the GTPγS binding assay can be used to identity bitter compounds and that hT2R761 functions as a human bitter taste receptor. The identified compounds can be used to provide bitterness to foods and beverages. Alternatively, these compounds can be used as agonists in assays for the identification of bitter blockers and modulators and other bitter compounds.

References

The references listed below as well as all references cited in the specification are incorporated herein by reference to the extent that they supplement, explain, provide a background for or teach methodology, techniques and/or compositions employed herein.

Adler E, Hoon M A, Mueller K L, Chandrashekar J, Ryba N J, Zuker C S (2000) A novel family of mammalian taste receptors. *Cell* 100(6): 693-702.

Altschul S F, Gish W, Miller W, Myers E W & Lipman D J (1990) Basic Local Alignment Search Tool. *J Mol Biol* 215:403-410.

Ausubel F, ed (1995) *Short Protocols in Molecular Biolog,* 3rd ed. Wiley, New York.

Barton G J (1998) Protein Sequence Alignment Techniques. *Acta Crystallogr D Biol Crystallogr* 54:1139-1146.

Bateman A, Birney E, Durbin R, Eddy S R, Howe K L & Sonnhammer E L (2000) The PFAM Protein Families Database. *Nucleic Acids Res* 28:263-266.

Batzer M A, Carlton J E & Deininger P L (1991) Enhanced Evolutionary PCR Using Oligonucleotides with Inosine at the 3'-Terminus. Nucleic Acids Res 19:5081.

Berridge & Irvine (1984) Inositol trisphosphate, a novel second messenger in cellular signal transduction. *Nature* 312: 315-321.

Bodanszky M (1993) *Principles of Peptide Synthesis,* 2nd rev. ed. Springer-Verlag, Berlin/New York.

Bourne H R, Sanders D A & McCormick F (1990) The GTPase superfamily: a conserved switch for diverse cell functions. *Nature* 348:125-132.

Bourne H R, Sanders D A & McCormick F (1991) *Nature* The GTPase superfamily: conserved structure and molecular mechanism. 349:117-127.

Brookes A J (1999) The Essence of SNPs. *Gene* 234:177-186.

Burge C & Karlin S (1997) Prediction of Complete Gene Structures in Human Genomic DNA. *J Mol Biol* 268:78-94.

Burge C B & Karlin S (1998) Finding the Genes in Genomic DNA. *Curr Opin Struct Biol* 8:346-354.

Capecchi M R (1989a) Altering the Genome by Homologous Recombination. *Science* 244:1288-1292.

Capecchi M R (1989b) Altering the Genome by Homologous Recombination. *Science* 244:1288-1292.

Chan D W (1996) *Immunoassay Automation: An Updated Guide to Systems.* Academic Press, San Diego, Calif., United States of America.

Chandrashekar J, Mueller K L, Hoon M A, Adler E, Feng L, Guo W, Zuker C S, Ryba N J (2000) T2Rs function as bitter taste receptors. *Cell* 100(6): 703-711.

Chiang L W (1998) Detection of Gene Expression in Single Neurons by Patch-Clamp and Single-Cell Reverse Transcriptase Polymerase Chain Reaction. *J Chromatogr A* 806:209-218.

Conner B J, Reyes A A, Morin C, Itakura K, Teplitz R L & Wallace R B (1983) Detection of Sickle Cell Beta S-Globin Allele by Hybridization with Synthetic Oligonucleotides. *Proc Natl Acad Sci USA* 80:278-282.

Costanzi E, Beccari T, Stinchi S, Bibi L, Hopwood J J & Orlacchio A (2000) Gene Encoding the Mouse Sulphamidase: cDNA Cloning, Structure, and Chromosomal Mapping. *Mamm Genome* 11:436-439.

Deisenhofer J, Epp 0, Miki K, Huber R & Michel H (1984) X-Ray Structure Analysis of a Membrane Protein Complex. Electron Density Map at 3 a Resolution and a Model of the Chromophores of the Photosynthetic Reaction Center from Rhodopseudomonas Viridis. *J Mol Biol* 180:385-398.

Felley-Bosco E, Ambs S, Lowenstein CJ, Keefer LK & Harris CC (1994) Constitutive expression of inducible nitric oxide synthase in human bronchial epithelial cells induces c-fos and stimulates the cGMP pathway. *Am J Resp Cell and Mol Biol* 11: 159-164.

Fewell J G, MacLaughlin F, Mehta V, Gondo M, Nicol F, Wilson E & Smith L C (2001) Gene Therapy for the Treatment of Hemophilia B Using PINC Formulated Plasmid Delivered to Muscle with Electroporation. *Mol Ther* 3:574-583.

Frank & Doring (1988) Simultaneous Multiple Peptide Synthesis Under Continuous Flow Conditions On Cellulose Paper Discs As Segmental Solid Supports. *Tetrahedron* 44:60316040.

Freshney R I (1987) Culture of Animal Cells: A Manual of Basic Technique, 2nd ed. A. R. Liss, New York.

Geysen H M, Rodda SJ, Mason TJ, Tribbick G & Schoofs PG (1987) Strategies for epitope analysis using peptide synthesis. *J Immun Meth* 102:259-274.

Glover DM & Hames BD (1995) *DNA Cloning: A Practical Approach*, 2nd ed. IRL Press at Oxford University Press, Oxford/New York.

Guo S W & Reed D R (2001) The genetics of phenylthiocarbamide perception. *Ann Hum Biol* 28:111-142.

Harlow E & Lane D (1988) *Antibodies: A Laboratory Manual*. Cold Spring Harbor Laboratory Press, Cold Spring Harbor, N.Y., United States of America.

Henikoff J G, Pietrokovski S, McCallum C M & Henikoff S (2000) Blocks-Based Methods for Detecting Protein Homology. *Electrophoresis* 21:1700-1706.

Henikoff S & Henikoff J G (1992) Amino Acid Substitution Matrices from Protein Blocks. *Proc Natl Acad Sci, USA* 89:10915-10919.

Henikoff S & Henikoff J G (2000) Amino Acid Substitution Matrices. *Adv Protein Chem* 54:73-97.

Homola J, Yee S & Gauglitz G (1999) Surface Plasmone Resonance Sensors: Review. *Sensors and Actuators B* 54:3-15.

Hoon M A, Adler E, Lindemeier J, Battey J F, Ryba N J P & Zuker C S (1995) "Functional expression of the taste specific G protein, alpha-gustducin." *Cell* 96629-636.

Huang C C, Novak W R, Babbitt P C, Jewett Al, Ferrin T E & Klein T E (2000) Integrated Tools for Structural and Sequence Alignment and Analysis. *Pac Symp Biocomput:* 230-241.

Hutchens & Yip (1993) New Desorption Strategies for the Mass Spectrometric Analysis of Macromolecules. *Rapid Communications in Mass Spectroscopy* 7:576-580.

Ishikawa E (1999) *Ultrasensitive and Rapid Enzyme Immunoassa*. Elsevier, Amsterdam/New York.

Jayaraman S, Teitler L, Skalski B & Verkman A S (1999) Long-Wavelength Iodide-Sensitive Fluorescent Indicators for Measurement of Functional CFTR Expression in Cells. *Am J Physiol* 277:C1 008-1018.

Joyner A L (1993) *Gene Targeting: A Practical Approach*. Oxford University Press, Oxford/New York.

Karlin S & Altschul S F (1993) Applications and Statistics for Multiple High-Scoring Segments in Molecular Sequences. *Proc Natl Acad Sci, USA* 90:5873-5877.

Kozal M J, Shah N, Shen N, Yang R, Fucini R, Merigan T C, Richman D D, Morris D, Hubbell E, Chee M & Gingeras T R (1996) Extensive polymorphisms observed in HIV-1 clade B protease gene using high-density oligonucleotide arrays. *Nat Med* 2(7):753-759.

Kyte J & Doolittle R F (1982) A Simple Method for Displaying the Hydropathic Character of a Protein. *J Mol Biol* 157:105-132.

Landegren U, Nilsson M & Kwok P Y (1998) Reading Bits of Genetic Information: Methods for Single-Nucleotide Polymorphism Analysis. *Genome Res* 8:769-776. Law (1996) *Immunoassay: A Practical Guide*. Taylor & Francis, London/Bristol, Pa., United States of America.

Lindemann B. (2001) Receptors and transduction in taste. *Nature* 413(6852): 219-225.

Maalouf G J, Xu W, Smith T F & Mohr S C (1998) Homology Model for the Ligand-Binding Domain of the Human Estrogen Receptor. *J Biomol Struct Dyn* 15:841-851.

Mak P, McDonnell D P, Weigel N L, Schrader W T & O'Malley B W (1989) Expression of Functional Chicken Oviduct Progesterone Receptors in Yeast (*Saccharomyces Cerevisiae*). *J Biol Chem* 264:21613-21618.

Manson MM (1992) *Immunochernical Protocols*. Humana Press, Totowa, N.J., United States of America Masseyeff R F, Albert WHW & Staines N (1993) *Methods of Immunological Analysis*.

VCH Verlagsgesellschaft; VCH Publishers, Weinheim (Federal Republic of Germany)/New York, N.Y. (United States of America).

Matsunami H, Montmpyeur J P, Buck L B (2000) A family of candidate taste receptors in human and mouse. *Nature* 404(6778): 601-604.

Merrifield (1963) *J Am Chem Soc* 85:2149-2154.

Mistili & Spector (1997) *Nat Biotech* 15:961-964.

Needleman S B & Wunsch C D (1970) A General Method Applicable to the Search for Similarities in the Amino Acid Sequence of Two Proteins. *J Mol Biol* 48:443453.

Nickerson D A, Kaiser R, Lappin S, Stewart J, Hood L & Landegren U (1990) Automated DNA Diagnostics Using an ELISA-Based Oligonucleotide Ligation Assay. *Proc Natl. Acad Sci, USA* 87:8923-8927.

Offermanns S & Simon M I (1995) G alpha 15 and G alpha 16 couple a wide variety of receptors to phospholipase C. *J Biol Chem* 270:15175-15180.

Ohtsuka E, Matsuki S, Ikehara M, Takahashi Y & Matsubara K (1985) An Alternative Approach to Deoxyoligonucleotides as Hybridization Probes by Insertion of Deoxyinosine at Ambiguous Codon Positions. *J Biol Chem* 260: 2605-2608.

Orita M, Iwahana H, Kanazawa H, Hayashi K & Sekiya T (1989) Detection of Polymorphisms of Human DNA by Gel Electrophoresis as Single-Strand Conformation Polymorphisms. *Proc Natl Acad Sci, USA* 86:2766-2770.

PCT International Publication No. WO 99/26966

PCT International Publication No. WO 01/18050

PCT International Publication No. WO 01/77676

Pitcher A Freedman N J & Lefkowitz R J (1998) G protein-coupled receptor kinases. *Annu Rev Biochem* 67:653-92.

Quandt K, Frech K, Karas H, Wingender E & Werner T (1995) Matind and Matinspector: New Fast and Versatile Tools for Detection of Consensus Matches in Nucleotide Sequence Data. *Nucleic Acids Res* 23:4878-4884.

Roberts L (1991) GRAIL Seeks out Genes Buried in DNA Sequence. *Science* 254:805.

Rossolini G M, Cresti S, Ingianni A, Cattani P, Riccio M L & Satta G (1994) Use of Deoxyinosine-Containing Primers Vs Degenerate Primers for Polymerase Chain Reaction Based on Ambiguous Sequence Information. *Mol Cell Probes* 8:91-98.

Ryba N J P & Trindelli R (1995) "A novel GTP-binding protein gamma-subunit, G gamma 8, is expressed during neurogenesis in the olfactory and vorneronasal neuroepithelia." *J Biol Chem* 270:6757-6767

Sambrook J, Sambrook E F & Maniatis F (1989) *Molecular Cloning: A Laboratory Manual.* Cold Spring Harbor Laboratory Press, Cold Spring Harbor, N.Y., United States of America.

Saqi M A, Wild D L & Hartshorn M J (1999) Protein Analyst—a Distributed Object Environment for Protein Sequence and Structure Analysis. *Bioinformatics* 15:521-522.

Schneider C H & Eberle A N (1993) *Pentides, 1992: Proceedings of the Twenty-Second European Peptide Symposium, Sep. 13-19, 1992. Interlaken Switzerland.* Escom, Leiden.

Schröder E & Lübke K (1965) *The Peptides.* Academic Press, New York.

Silhavy TJ, Berman ML, Enquist LW & Cold Spring Harbor Laboratory. (1984) *Experiments with Gene Fusions.* Cold Spring Harbor Laboratory, Cold Spring Harbor, N.Y., United States of America.

Smith T F & Waterman M (1981) Comparison of Biosequences. *Adv Appl Math* 2:482-489.

Stoneking M, Hedgecock D, Higuchi R G, Vigilant L & Erlich H A (1991) Population Variation of Human mtDNA Control Region Sequences Detected by Enzymatic Amplification and Sequence-Specific Oligonucleotide Probes. *Am J Hum Genet* 48:370-382.

Taylor G, Vimr E, Garman E & Laver G (1992) Purification, Crystallization and Preliminary Crystallographic Study of Neuraminidase from Vibrio *Cholerae* and *Salmonella Typhimurfum* Lt2. *J Mol Biol* 226:1287-1290.

Tijssen (1993) *Laboratory Technigues in Biochemistry and Molecular Biology-Hybridization with Nucleic Acid Probes.* Elsevier, New York.

U.S. Pat. No. 4,115,538
U.S. Pat. No. 4,196,265
U.S. Pat. No. 4,455,842
U.S. Pat. No. 4,554,101
U.S. Pat. No. 4,736,866
U.S. Pat. No. 4,946,778
U.S. Pat. No. 5,091,513
U.S. Pat. No. 5,132,405
U.S. Pat. No. 5,162,215
U.S. Pat. No. 5,223,409
U.S. Pat. No. 5,260,203
U.S. Pat. No. 5,264,563
U.S. Pat. No. 5,436,128
U.S. Pat. No. 5,489,742
U.S. Pat. No. 5,498,538
U.S. Pat. No. 5,550,316
U.S. Pat. No. 5,573,933
U.S. Pat. No. 5,629,145
U.S. Pat. No. 5,614,396
U.S. Pat. No. 5,625,125
U.S. Pat. No. 5,648,061
U.S. Pat. No. 5,650,489
U.S. Pat. No. 5,667,988
U.S. Pat. No. 5,677,427
U.S. Pat. No. 5,702,892
U.S. Pat. No. 5,741,957
U.S. Pat. No. 5,738,996
U.S. Pat. No. 5,747,334
U.S. Pat. No. 5,756,291
U.S. Pat. No. 5,776,859
U.S. Pat. No. 5,780,225
U.S. Pat. No. 5,780,242
U.S. Pat. No. 5,824,483
U.S. Pat. No. 5,834,228
U.S. Pat. No. 5,840,479
U.S. Pat. No. 5,858,670
U.S. Pat. No. 5,872,011
U.S. Pat. No. 5,892,019
U.S. Pat. No. 5,922,254
U.S. Pat. No. 5,948,635
U.S. Pat. No. 6,004,808
U.S. Pat. No. 6,057,098
U.S. Pat. No. 6,107,059
U.S. Pat. No. 6,140,123
U.S. Pat. No. 6,156,511
U.S. Pat. No. 6,168,912
U.S. Pat. No. 6,174,708
U.S. Pat. No. 6,176,089
U.S. Pat. No. 6,180,348
U.S. Pat. No. 6,190,700
U.S. Pat. No. 6,214,553
U.S. Pat. No. 6,255,059
U.S. Pat. No. 6,403,305

Walker M R & Rapley R (1993) *Molecular and Antibody Probes in Diagnosis.* Wiley, Chichester/New York.

Wang D G, Fan J B, Siao C J, Berno A, Young P, Sapolsky R, Ghandour G, Perkins N, Winchester E, Spencer J, Kruglyak L, Stein L, Hsie L, Topaloglou T, Hubbell E, Robinson E, Mittmann M, Morris MS, Shen N, Kilburn D, Rioux J, Nusbaum C, Rozen S, Hudson T J, Lander E S & et al. (1998) Large-Scale Identification, Mapping, and Genotyping of Single-Nucleotide Polymorphisms in the Human Genome. *Science* 280:1077-1082.

Weiss M S, Wacker T, Weckesser J, Welte W & Schulz G E (1990) The Three-Dimensional Structure of Porin from Rhodobacter Capsulatus at 3 a Resolution. *FEBS Lett* 267: 268-272.

Wilkie T M, Scherle P A, Strathmann M P, Slepak V Z & Simon M I (1991) Characterization of G-protein alpha subunits in the Gq class: expression in murine tissues and in stromal and hematopoietic cell lines. *Proc Natl Acad Sci, USA* 88:10049-10053.

Wong G T, Gannon K S, Margolskee R F (1996) Transduction of bitter and sweet taste by gustducin. *Nature* 381(6585): 796-800.

Worrall T A, Cotter R J & Woods A S (1998) Purification of Contaminated Peptides and Proteins on Synthetic Membrane Surfaces for Matrix-Assisted Laser Desorption/Ionization Mass Spectrometry. *Anal Chem* 70:750-756.

Wyckoff H W, Hirs C H W & Timasheff S N (1985) *Diffraction Methods for Biological Macromolecules.* Academic Press, Orlando, Fla., United States of America.

Yuan B, Thomas J P, von Kodolitsch Y & Pyeritz R E (1999) Comparison of Heteroduplex Analysis, Direct Sequencing, and Enzyme Mismatch Cleavage for Detecting Mutations in a Large Gene, FBN1. *Hum Mutat* 14:440-446.

It will be understood that various details of the invention can be changed without departing from the scope of the invention. Furthermore, the foregoing description is for the purpose of illustration only, and not for the purpose of limitation—the invention being defined by the claims appended hereto.

What is claimed is:

1. An isolated nucleic acid sequence that is selected from the group consisting of:
   (i) a nucleic acid sequence that encodes a polypeptide having at least 95% sequence identity to the polypeptide of SEQ ID NO:2 and which specifically binds to a bitter ligand that specifically binds the T2R76 polypeptide of SEQ ID NO:2;
   (ii) a nucleic acid sequence that has the sequence of SEQ ID NO:1; and
   (iii) a nucleic acid sequence that hybridizes under high stringency conditions to the nucleic acid sequence of SEQ ID NO:1 wherein high stringency conditions are incubating for 15 minutes in 0.1×SSC at 65 degrees C. and which isolated nucleic acid sequence encodes a taste receptor polypeptide that specifically binds to a bitter ligand that specifically binds to the T2R76 polypeptide of SEQ ID NO:2, and further wherein said isolated nucleic acid sequence of part (i), (ii) or (iii) is operatively linked to a heterologous promoter that provides for the expression thereof in a recombinant host cell containing said isolated nucleic acid sequence.

2. The isolated nucleic acid sequence of claim 1 which encodes a polypeptide that possesses greater than 95% sequence identity to the polypeptide of SEQ ID NO:2 and which specifically binds to at least one bitter ligand specifically bound by the T2R76 polypeptiide of SEQ ID NO: 2.

3. The isolated nucleic acid sequence of claim 1 which encodes a polypeptide having at least 99% sequence identity with the T2R76 polypeptide of SEQ ID NO: 2 and which polypeptide specifically binds at least one bitter ligand specifically bound by the T2R76 polypeptide of SEQ ID NO:2.

4. The isolated nucleic acid sequence of claim 1 which comprises the sequence of SEQ ID NO: 1.

5. The isolated nucleic acid sequence of claim 1 which encodes a polypeptide comprising the sequence of SEQ ID NO: 2.

6. The isolated nucleic acid sequence of claim 1 which is selected from the group consisting of an mRNA, cRNA, cDNA and genomic sequence.

7. The isolated nucleic acid sequence of claim 1 which is operatively linked to an inducible promoter.

8. The isolated nucleic acid sequence of claim 1 which is operatively linked to a constitutive promoter.

9. An isolated recombinant cell containing the isolated nucleic acid sequence of claim 1 wherein said cell further expresses a sequence encoding a G protein that functionally couples to the T2R76 polypeptide encoded by said isolated sequence.

10. The cell of claim 9 wherein said G protein is a promiscuous G protein.

11. The cell of claim 9 wherein said G protein is selected from the group consisting of Galpha15, Galpha16, Gq, gustducin and transducin.

12. The isolated nucleic acid molecule of claim 1 which further comprises a sequence that encodes a detectable marker.

13. An isolated recombinant host cell that has been transfected or transformed with an isolated nucleic acid sequence according to claim 1.

14. The isolated host cell of claim 13 which is a eukaryotic cell.

15. The isolated recombinant host cell of claim 13 which is selected from the group consisting of a mammalian cell, an insect cell, an amphibian cell, a bacterial cell, and a yeast cell.

16. The isolated recombinant host cell of claim 13 which is selected from the group consisting of an HEK-293 cell, CV-1 cell, HeLa cell, COS cell and a Sf9 cell.

17. The isolated recombinant host cell of claim 13 which is a human cell.

18. The isolated recombinant host cell of claim 13 which is a HEK-293 cell.

19. The isolated recombinant host cell of claim 17 which further expresses a G protein that functionally couples with the T2R76 polypeptide encoded by said isolated nucleic acid sequence.

20. The isolated recombinant host cell of claim 13 which further expresses another T2R polypeptide.

* * * * *

SEQUENCE LISTING

<160> NUMBER OF SEQ ID NOS: 2

<210> SEQ ID NO 1
<211> LENGTH: 957
<212> TYPE: DNA
<213> ORGANISM: Homo sapiens
<220> FEATURE:
<221> NAME/KEY: CDS
<222> LOCATION: (1)..(954)

<400> SEQUENCE: 1

```
atg aat gga gac cac atg gtt cta gga tct tcg gtg act gac aag aag      48
Met Asn Gly Asp His Met Val Leu Gly Ser Ser Val Thr Asp Lys Lys
 1               5                  10                  15 gcc atc atc ttg gtt acc att tta ctc ctt tta cgc ctg gta gca ata      96
Ala Ile Ile Leu Val Thr Ile Leu Leu Leu Leu Arg Leu Val Ala Ile
             20                  25                  30 gca ggc aat ggc ttc atc act gct gct ctg ggc gtg gag tgg gtg cta     144
Ala Gly Asn Gly Phe Ile Thr Ala Ala Leu Gly Val Glu Trp Val Leu
         35                  40                  45 cgg aga atg ttg ttg cct tgt gat aag tta ttg gtt agc cta ggg gcc     192
Arg Arg Met Leu Leu Pro Cys Asp Lys Leu Leu Val Ser Leu Gly Ala
     50                  55                  60 tct cgc ttc tgt ctg cag tca gtg gta atg ggt aag acc att tat gtt     240
Ser Arg Phe Cys Leu Gln Ser Val Val Met Gly Lys Thr Ile Tyr Val
 65                  70                  75                  80 ttg cat ccg atg gcc ttc cca tac aac cct gta ctg cag ttt cta         288
Phe Leu His Pro Met Ala Phe Pro Tyr Asn Pro Val Leu Gln Phe Leu
                 85                  90                  95 gct ttc cag tgg gac ttc ctg aat gct gcc acc tta tgg tcc tct acc     336
Ala Phe Gln Trp Asp Phe Leu Asn Ala Ala Thr Leu Trp Ser Ser Thr
            100                 105                 110 tgg ctc agt gtc ttc tat tgt gtg aaa att gct acc ttc acc cac cct     384
Trp Leu Ser Val Phe Tyr Cys Val Lys Ile Ala Thr Phe Thr His Pro
        115                 120                 125 gtc ttc ttc tgg cta aag cac aag ttg tct ggg tgg cta cca tgg atg     432
Val Phe Phe Trp Leu Lys His Lys Leu Ser Gly Trp Leu Pro Trp Met
    130                 135                 140 ctc ttc agc tct gta ggg ctc tcc agc ttc acc acc att cta ttt ttc     480
Leu Phe Ser Ser Val Gly Leu Ser Ser Phe Thr Thr Ile Leu Phe Phe
145                 150                 155                 160 ata ggc aac cac aga atg tat cag aac tat tta agg aac cat cta caa     528
Ile Gly Asn His Arg Met Tyr Gln Asn Tyr Leu Arg Asn His Leu Gln
                165                 170                 175 cct tgg aat gtc act ggc gat agc ata cgg agc tac tgt gag aaa ttc     576
Pro Trp Asn Val Thr Gly Asp Ser Ile Arg Ser Tyr Cys Glu Lys Phe
            180                 185                 190 tat ctc ttc cct cta aaa atg att act tgg aca atg ccc act gct gtc     624
Tyr Leu Phe Pro Leu Lys Met Ile Thr Trp Thr Met Pro Thr Ala Val
        195                 200                 205 ttt ttc att tgc atg att ttg ctc atc aca tct ctg gga aga cac agg     672
Phe Phe Ile Cys Met Ile Leu Leu Ile Thr Ser Leu Gly Arg His Arg
    210                 215                 220 aag aag gct ctc ctt aca acc tca gga ttc cga gag ccc agt gtg cag     720
Lys Lys Ala Leu Leu Thr Thr Ser Gly Phe Arg Glu Pro Ser Val Gln
225                 230                 235                 240 gca cac ata aag gct ctg ctg gct ctc tct ttt gcc atg ctc ttc         768
Ala His Ile Lys Ala Leu Leu Ala Leu Leu Ser Phe Ala Met Leu Phe
                245                 250                 255
```

```
atc tca tat ttc ctg tca ctg gtg ttc agt gct gca ggt att ttt cca    816
Ile Ser Tyr Phe Leu Ser Leu Val Phe Ser Ala Ala Gly Ile Phe Pro
        260                 265                 270 cct ctg gac ttt aaa ttc tgg gtg tgg gag tca gtg att tat ctg tgt    864
Pro Leu Asp Phe Lys Phe Trp Val Trp Glu Ser Val Ile Tyr Leu Cys
            275                 280                 285 gca gca gtt cac ccc atc att ctg ctc ttc agc aac tgc agg ctg aga    912
Ala Ala Val His Pro Ile Ile Leu Leu Phe Ser Asn Cys Arg Leu Arg
        290                 295                 300 gct gtg ctg aag agt cgy cgt tcc tca agg tgt ggg aca cct tga        957
Ala Val Leu Lys Ser Arg Arg Ser Ser Arg Cys Gly Thr Pro
305                 310                 315

<210> SEQ ID NO 2
<211> LENGTH: 318
<212> TYPE: PRT
<213> ORGANISM: Homo sapiens

<400> SEQUENCE: 2

Met Asn Gly Asp His Met Val Leu Gly Ser Ser Val Thr Asp Lys Lys
 1               5                  10                  15

Ala Ile Ile Leu Val Thr Ile Leu Leu Leu Arg Leu Val Ala Ile
            20                  25                  30

Ala Gly Asn Gly Phe Ile Thr Ala Ala Leu Gly Val Glu Trp Val Leu
        35                  40                  45

Arg Arg Met Leu Leu Pro Cys Asp Lys Leu Leu Val Ser Leu Gly Ala
    50                  55                  60

Ser Arg Phe Cys Leu Gln Ser Val Val Met Gly Lys Thr Ile Tyr Val
65                  70                  75                  80

Phe Leu His Pro Met Ala Phe Pro Tyr Asn Pro Val Leu Gln Phe Leu
                85                  90                  95

Ala Phe Gln Trp Asp Phe Leu Asn Ala Ala Thr Leu Trp Ser Ser Thr
            100                 105                 110

Trp Leu Ser Val Phe Tyr Cys Val Lys Ile Ala Thr Phe Thr His Pro
        115                 120                 125

Val Phe Phe Trp Leu Lys His Lys Leu Ser Gly Trp Leu Pro Trp Met
    130                 135                 140

Leu Phe Ser Ser Val Gly Leu Ser Ser Phe Thr Thr Ile Leu Phe Phe
145                 150                 155                 160

Ile Gly Asn His Arg Met Tyr Gln Asn Tyr Leu Arg Asn His Leu Gln
                165                 170                 175

Pro Trp Asn Val Thr Gly Asp Ser Ile Arg Ser Tyr Cys Glu Lys Phe
            180                 185                 190

Tyr Leu Phe Pro Leu Lys Met Ile Thr Trp Thr Met Pro Thr Ala Val
        195                 200                 205

Phe Phe Ile Cys Met Ile Leu Leu Ile Thr Ser Leu Gly Arg His Arg
    210                 215                 220

Lys Lys Ala Leu Leu Thr Thr Ser Gly Phe Arg Glu Pro Ser Val Gln
225                 230                 235                 240

Ala His Ile Lys Ala Leu Leu Ala Leu Leu Ser Phe Ala Met Leu Phe
                245                 250                 255

Ile Ser Tyr Phe Leu Ser Leu Val Phe Ser Ala Ala Gly Ile Phe Pro
            260                 265                 270

Pro Leu Asp Phe Lys Phe Trp Val Trp Glu Ser Val Ile Tyr Leu Cys
        275                 280                 285
```

```
Ala Ala Val His Pro Ile Ile Leu Leu Phe Ser Asn Cys Arg Leu Arg
    290                 295                 300

Ala Val Leu Lys Ser Arg Arg Ser Ser Arg Cys Gly Thr Pro
305                 310                 315
```